US009561249B2

(12) United States Patent
Kevil et al.

(10) Patent No.: US 9,561,249 B2
(45) Date of Patent: Feb. 7, 2017

(54) PHARMACEUTICAL FORMULATIONS OF NITRITE AND USES THEREOF

(71) Applicant: TheraVasc Inc., Cleveland, OH (US)

(72) Inventors: Christopher Kevil, Shreveport, LA (US); Kyle Chan, San Diego, CA (US); Amol Soin, Centerville, OH (US)

(73) Assignee: TheraVasc Inc., Cleveland, OH (US)

( * ) Notice: Subject to any disclaimer, the term of this patent is extended or adjusted under 35 U.S.C. 154(b) by 0 days.

(21) Appl. No.: 14/626,571

(22) Filed: Feb. 19, 2015

(65) Prior Publication Data

US 2015/0196588 A1 Jul. 16, 2015

Related U.S. Application Data

(63) Continuation of application No. PCT/US2014/017432, filed on Feb. 20, 2014.

(Continued)

(51) Int. Cl.
*A61K 33/00* (2006.01)
*A61K 9/20* (2006.01)
(Continued)

(52) U.S. Cl.
CPC ............ *A61K 33/00* (2013.01); *A61K 9/0019* (2013.01); *A61K 9/06* (2013.01); *A61K 9/08* (2013.01);
(Continued)

(58) Field of Classification Search
CPC ............ A61K 33/00; A61K 9/20; A61K 9/48; A61K 45/06; A61K 9/28; A61K 33/08
See application file for complete search history.

(56) References Cited

U.S. PATENT DOCUMENTS

| 4,650,484 A | 3/1987 | Shaw et al. |
| 5,122,384 A | 6/1992 | Paradissis et al. |

(Continued)

FOREIGN PATENT DOCUMENTS

| EP | 1 336 602 A1 | 8/2003 |
| JP | 2005-501069 A | 1/2005 |

(Continued)

OTHER PUBLICATIONS

Allen et al., "Plasma Nitrite Response and Arterial Reactivity Differentiate Vascular Health and Performance," Nitric Oxide, 20:231-237 (2009).

(Continued)

*Primary Examiner* — Lakshmi Channavajjala
(74) *Attorney, Agent, or Firm* — Clark & Elbing LLP

(57) ABSTRACT

The present invention relates to pharmaceutical compositions of nitrites such as inorganic nitrites, or any pharmaceutically acceptable salts, solvates, or prodrugs thereof, and the medical use of these compositions. The pharmaceutical compositions, which can be formulated for oral administration, can provide immediate release or extended release of the nitrite ion ($NO_2^-$). The pharmaceutical compositions of the invention are useful, for example, for modulating brain function, in particular improving mood and/or psychological state, in the treatment of disorders of brain development, and in the treatment and/or reduction of pain.

15 Claims, 3 Drawing Sheets

Related U.S. Application Data

(60) Provisional application No. 61/767,017, filed on Feb. 20, 2013.

(51) Int. Cl.
  *A61K 9/48*  (2006.01)
  *A61K 45/06*  (2006.01)
  *A61K 9/06*  (2006.01)
  *A61K 9/08*  (2006.01)
  *A61K 9/00*  (2006.01)
  *A61K 9/28*  (2006.01)

(52) U.S. Cl.
  CPC ............... *A61K 9/20* (2013.01); *A61K 45/06* (2013.01); *A61K 9/0014* (2013.01); *A61K 9/28* (2013.01); *A61K 9/48* (2013.01)

(56) References Cited

U.S. PATENT DOCUMENTS

| | | |
|---|---|---|
| 5,489,610 A | 2/1996 | Fung et al. |
| 5,648,101 A | 7/1997 | Tawashi |
| 5,692,500 A | 12/1997 | Gaston-Johansson |
| 5,770,645 A | 6/1998 | Stamler et al. |
| 5,994,444 A | 11/1999 | Trescony et al. |
| 6,641,839 B1 | 11/2003 | Geoghegan et al. |
| 6,709,681 B2 | 3/2004 | Benjamin et al. |
| 6,962,717 B1 | 11/2005 | Huber et al. |
| 7,371,415 B1 | 5/2008 | Wuh et al. |
| 2003/0219495 A1 | 11/2003 | Juneau et al. |
| 2004/0006140 A1 | 1/2004 | Kaesemeyer |
| 2006/0083824 A1 | 4/2006 | Manning et al. |
| 2006/0125714 A1 | 6/2006 | Miller |
| 2006/0182815 A1 | 8/2006 | Gladwin et al. |
| 2007/0010571 A1 | 1/2007 | Garvey et al. |
| 2007/0154569 A1 | 7/2007 | Gladwin et al. |
| 2009/0196930 A1 | 8/2009 | Surber et al. |
| 2009/0297634 A1 | 12/2009 | Friedman et al. |
| 2010/0092441 A1 | 4/2010 | Lundberg et al. |
| 2010/0203172 A1 | 8/2010 | Sherman et al. |
| 2010/0247682 A1 | 9/2010 | Gladwin et al. |
| 2011/0086069 A1 | 4/2011 | Kevil et al. |
| 2011/0311653 A1 | 12/2011 | Kevil et al. |
| 2012/0237617 A1 | 9/2012 | Kevil |
| 2013/0209584 A1 | 8/2013 | Kevil et al. |
| 2014/0127329 A1 | 5/2014 | Giordano et al. |
| 2014/0242194 A1* | 8/2014 | Kevil ............................ 424/718 |
| 2015/0110899 A1* | 4/2015 | Kevil et al. ................... 424/718 |

FOREIGN PATENT DOCUMENTS

| | | |
|---|---|---|
| JP | 2007-528852 A | 10/2007 |
| WO | WO-94/01103 A1 | 1/1994 |
| WO | WO-00/03725 A1 | 1/2000 |
| WO | WO-00/53193 A1 | 9/2000 |
| WO | WO-03/013489 A1 | 2/2003 |
| WO | WO-2005/004884 A2 | 1/2005 |
| WO | WO-2005/007173 A1 | 1/2005 |
| WO | WO-2006/128032 A2 | 11/2006 |
| WO | WO-2007/116102 A2 | 10/2007 |
| WO | WO-2008/105730 A1 | 9/2008 |
| WO | WO-2008/105731 A1 | 9/2008 |
| WO | WO-2008/153762 A2 | 12/2008 |
| WO | WO-2009/065142 A2 | 5/2009 |
| WO | WO-2010/036236 A1 | 4/2010 |
| WO | WO-2010/147742 A2 | 12/2010 |
| WO | WO-2011/047161 A1 | 4/2011 |
| WO | WO-2012/052561 A2 | 4/2012 |
| WO | WO-2012/135623 A1 | 10/2012 |
| WO | WO-2012/142413 A2 | 10/2012 |

OTHER PUBLICATIONS

Blood et al., "In vitro and in vivo kinetic handling of nitrite in blood: Effects of varying hemoglobin oxygen saturation," Am J Physiol Heart Circ Physiol. 293:H1508-H1517 (2007).
Bryan et al., "Dietary nitrite supplementation protects against myocardial ischemia-reperfusion injury," Proc Natl Acad Sci USA. 104(48):19144-9 (2007).
Combet et al., "Diet, gastric nitrosation and stomach cancer," Comp Biochem Physiol. Part A 146:S61 (2007) (Abstract only).
Contreras, et al. "The role of nitric oxide in the post-ischemic revascularization process," Pharmacol Ther. 112(2):553-63 (2006).
Cosby et al., "Nitrite reduction to nitric oxide by deoxyhemoglobin vasodilates the human circulation," Nat Med. 9(12):1498-1505 (2003).
Croft et al., "Ultrastructural studies of wound healing in mouse skin," J Anat. 106:63-77 (1970).
Dejam et al., "Nitrite infusion in humans and nonhuman primates: Endocrine effects, pharmacokinetics, and tolerance formation," Circulation. 116:1821-1831 (2007).
Duranski et al., "Cytoprotective effects of nitrite during in vivo ischemia-reperfusion of the heart and liver," J Clin Invest. 115(5):1232-40 (2005).
Greenberg, et al., "Nitro containing L-arginine analogs interfere with assays for nitrate and nitrite," Life Sci. 57(21):1949-61 (1995).
Greenway et al., "Single-dose pharmacokinetics of different oral sodium nitrite formulations in diabetes patients," Diabetes Technol Ther. 14(7):552-560 (2012).
Grosse et al., "Carcinogenicity of nitrate, nitrite, and cyanobacterial peptide toxins," Lancet Oncol. 7(8):628-629 (2006).
Hunault et al., "Bioavailability of sodium nitrite from an aqueous solution in healthy adults," available at doi: 10.1016/j.toxlet.2009.06.865 Jul. 1, 2009, published in final edited form as: Toxic Lett. 190(1):48-53 (2009) (6 pages).
"In High Blood Pressure," The Canadian Medical Association Journal p. xliii, (1928).
Jacoby et al., "Acute myocardial infarction in the diabetic patient: Pathophysiology, clinical course and prognosis," J Am Coll Cardiol. 20(3):736-44 (1992).
Jadeski et al., "Nitric oxide synthase inhibition by N(G)-nitro-L-arginine methyl ester inhibits tumor-induced angiogenesis in mammary tumors," Am J Pathol. 155(4):1381-90 (1999).
Jung et al., "Early intravenous infusion of sodium nitrite protects brain against in vivo ischemia-reperfusion reperfusion injury." Stroke. 37(11):2744-50 (2006).
Kenjale et al., "Dietary nitrate supplementation enhances exercise performance in peripheral arterial disease," J Appl Physiol. 110:1582-1591 (2011).
Kevil et al., "Inorganic nitrite therapy: historical perspective and future directions," Free Radic Biol Med. 51(3):576-93 (2011).
Kleinbongard et al., "Plasma nitrite concentrations reflect the degree of endothelial dysfunction in humans," Free Radic Biol Med. 40(2):295-302 (2006).
Kohn et al., "Pharmacokinetics of sodium nitrite-induced methemoglobinemia in the rat," Drug Metab Dispos. 30(6):676-683 (2002).
Kumar et al., "Chronic sodium nitrite therapy augments ischemia-induced angiogenesis and arteriogenesis," Proc Nat Acad Sci USA. 105(21):7540-7545 (2008).
Mazzone et al., "Drug discovery: a lifeline for suffocating tissues," Nature. 453:1194-1195 (2008).
Modin et al., "Nitrite-derived nitric oxide: a possible mediator of acidic-metabolic' vasodilation," Acta Physiol Scand. 171:9-16 (2001).
Moshage et al., "Nitrite and nitrate determinations in plasma: A critical evaluation," Clin Chem. 41(6):892-896 (1995).
Namba et al., "Angiogenesis induced by endothelial nitric oxide synthase gene through vascular endothelial growth factor expression in a rat hindlimb ischemia model," Circulation. 108:2250-2257 (2003).
"Peripheral arterial disease in people with diabetes," Diabetes Care 26(12):3333-3341 (2003).

(56) References Cited

OTHER PUBLICATIONS

Presley et al., "Acute effect of a high nitrate diet on brain perfusion in older adults," available at doi: 10.1016/j.niox.2010.10.002 Oct. 15, 2010, published in final edited form as: Nitric Oxide. 24(1):34-42 (2011) (9 pages).
Rikitake et al., "Involvement of endothelial nitric oxide in sphingosine-1-phosphate-induced angiogenesis," Arterioscler Thromb Vasc Biol. 22(1):108-14 (2002).
Sun et al., "Induction of angiogenesis by heat shock protein 90 mediated by protein kinase Akt and endothelial nitric oxide synthase," Arterioscler Thromb Vasc Biol. 24(12):2238-44 (2004).
Sun et al., "Measurement of nitric oxide production in biological systems by using griess reaction assay," Sensors 3:276-284 (2003).
Tsuchiya et al., "Nitrite is an alternative source of NO in vivo," Am J Physiol Heart Circ Physiol. 288 (5):H2163-70 (2005).
Tripathi et al., "Effect of superoxide dismutase and acidified sodium nitrite on infarct size following ischemia and reperfusion in dogs," Indian J Physiol Pharmacol. 41(3):248-56 (Abstract Only) (1997).
Van Velzen et al., "The oral bioavailability of nitrate from nitrate-rich vegetables in humans," Toxicol Lett. 181:177-181 (2008).
Verma et al., "A self-fulfilling prophecy: C-reactive protein attenuates nitric oxide production and inhibits angiogenesis," Circulation. 106(8):913-9 (2002).
Vitecek et al., "Arginine-based inhibitors of nitric oxide synthase: therapeutic potential and challenges," Mediators Inflamm. 2012(318087):1-22 (2012).
Weller et al., "The effects of topical treatment with acidified nitrite on wound healing in normal and diabetic mice," Nitric Oxide. 15(4):395-9 (2006).
Notice of Judgment Case No. 4151. Adulteration and misbranding of Natrico tablets. *U.S.* v. *140 Bottles* p. 147 (1954).
Notices of Judgment Case 2310, Adulteration and alleged misbranding of drug tablets. *U.S.* v. *Charles H. Dietz, Inc*. p. 47-48 (1949).
International Search Report and Written Opinion for International Patent Application No. PCT/US14/17432, dated Aug. 11, 2014 (14 pages).
International Preliminary Report on Patentability and Written Opinion for International Application No. PCT/US2014/017432, issued Aug. 25, 2015 and mailed Sep. 3, 2015 (6 pages).
Extended European Search Report for European Application No. 14754330.0, mailed Sep. 21, 2016 (6 pages).

* cited by examiner

PHARMACEUTICAL FORMULATIONS OF NITRITE AND USES THEREOF

BACKGROUND OF THE INVENTION

The present invention relates to pharmaceutical compositions of nitrites and the medical use of these compositions.

Nitric oxide (NO) serves as a neurotransmitter between nerve cells and has a general role in redox signaling. Unlike most other neurotransmitters that only transmit information from a presynaptic to a postsynaptic neuron, the small, uncharged, and fat-soluble nitric oxide molecule can diffuse widely and readily enters cells. Thus, it can act on several nearby neurons, even on those not connected by a synapse. At the same time, the short half-life of NO means that such action will be restricted to a limited area, without the necessity for enzymatic breakdown or cellular reuptake. NO is also highly reactive with other free radicals, lipids, and proteins.

NO-cGMP cascade is involved in learning and memory through the maintenance of long-term potentiation (LTP). Thus, NO is an important regulator and mediator of many processes in the brain and a balance in NO levels is critical in maintaining healthy signaling and brain development, and/or maintaining a balance in psychological state.

The role of NO has also been implicated in pain, however it remains unclear as to whether inhibition of NO or production of NO is beneficial in the treatment of pain. In some studies, it has been proposed that several pain-related pathways benefit from the production of NO. In particular, the blood-flow pathway, which is normalized in the presence of NO, may help to decrease ischemic pain; the nerve transmission pathway, which decreases the irritation of the nerves in the synovium, bone, and soft tissues; the opioid receptor pathway, which might stimulate the body's normal pain reduction pathways; and the anti-inflammation pathway. Other studies proposed that the inhibition of NO is beneficial in the treatment of pain. In these studies, NO is believed to be involved in the activation of cyclooxygenase 1 (COX-1) and regulation of cyclooxygenase 2 (COX-2) expression in inflammatory responses to increase prostaglandin release thereby inducing peripheral hyperalgesia and inflammation. NO generated by activation of N-methyl-D-aspartate (NMDA) receptors has been implicated in synaptic plasticity and many of these mechanisms are involved in central sensitization, a common problem in chronic pain. Certain studies have also suggested that NO mediates the peripheral and central anti-nociceptive effects of analgesic compounds such as opioids, and nonsteroidal anti-inflammatory drugs.

Accordingly, there is a continuing need to understand the biological functions of NO and to investigate therapeutic strategies that provide a source of NO for maintaining normal brain functions and for the treatment and/or reduction of pain.

SUMMARY OF THE INVENTION

In general, in a first aspect, the invention features a method of treating or reducing pain, that includes administering to a subject in need thereof a pharmaceutical composition including an effective amount of inorganic nitrite or a pharmaceutically acceptable salt thereof, and a pharmaceutically acceptable excipient. In a particular embodiment, the invention features a method of treating or reducing neuropathic pain, the method including administering the pharmaceutical composition described above. In a preferred embodiment, the invention features a method of treating or reducing diabetic peripheral neuropathy, that includes administering to the subject the pharmaceutical composition as described above.

In a second aspect, the invention further includes monitoring whether the subject experiences reduced pain, wherein reduced pain is measured as a decrease in pain intensity, frequency, duration, and/or improvements in quality of life.

In some embodiments, the subject has type 1 or type 2 diabetes. In other embodiments, subject does not have a condition associated with chronic ischemia. In yet another embodiment, the subject has a predisposition to, is diagnosed with, or has chronic pain.

In any of the foregoing aspects, the chronic pain is associated with lower back pain, arthritis, headache, multiple sclerosis, fibromyalgia, shingles, nerve damage, or cancer. In some instances the pain is neuropathic pain, inflammatory pain, nociceptive pain, functional pain, musculo-skeletal pain, or central nervous system pain. In certain embodiments, the neuropathic pain is diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathys, mono-neuropathies, or central pain syndrome. In a preferred embodiment, the pain is diabetic peripheral neuropathy.

In a third aspect, the invention features a method of treating a mood disorder or a disorder of brain development, the method including administering to a subject in need thereof a pharmaceutical composition including an effective amount of inorganic nitrite or a pharmaceutically acceptable salt thereof, and a pharmaceutically acceptable excipient.

In some embodiments, the mood disorder is selected from the group consisting of: major depressive disorders, depressive disorders, bipolar disorders, substance induced mood disorders, alcohol induced mood disorders, and benzodiazepine induced mood disorders. In other embodiments, the disorder of brain development is selected from the group consisting of: impairment of learning and memory, autistic disorder, Rett syndrome, childhood disintegrative disorder, pervasive developmental disorder-not otherwise specified (PDD-NOS), and Asperger syndrome.

In any of the foregoing aspects, the pharmaceutical composition includes from about 10 mg to about 100 mg or from about 20 mg to about 200 mg of inorganic nitrite, wherein the inorganic nitrite is $NaNO_2$, or $KNO_2$. In preferred embodiments, the inorganic nitrite is $NaNO_2$. In some aspects, the pharmaceutical composition is administered with a second agent, wherein the second agent is selected from the group consisting of: a non-steroidal anti-inflammatory drug (NTHE), a corticosteroid, acetaminophen, an opioid, a muscle relaxant, an anti-anxiety drug, an antidepressant, an anti-convulsant drug, an antipsychotic, an antiepileptic drug, a selective serotonin reuptake inhibitor (SSRI), a norepinephrin inhibitor, and a mood stabilizer.

In one embodiment, the pharmaceutical composition is administered one or more times a day. In a second embodiment, the pharmaceutical composition is administered for at least two to twenty days. In a third embodiment, the administration occurs for at least two days, at least three days, at least four days, at least five days, at least six days, at least seven days, at least ten days, or at least fifteen days. In a fourth embodiment, the dose is about 0.5 to about 2000 µg/kg; about 0.5 to about 1000 µg/kg; about 0.5 µg/kg to about 500 µg/kg; about 0.5 µg/kg to about 250 µg/kg; about 0.5 µg/kg to about 100 µg/kg; or about 0.5 µg/kg to about 50

µg/kg. In a preferred embodiment, the dose is about 165 µg/kg; about 16.5 µg/kg; or about 8.25 µg/kg.

In certain embodiments, the pharmaceutical composition is formulated for topical, enteral, or parenteral administration. In other embodiments, the pharmaceutical composition is formulated as a solid dosage form for oral administration. In preferred embodiments, the pharmaceutical composition is a tablet or capsule.

In any of the foregoing embodiments, the pharmaceutical composition includes a pharmaceutically acceptable excipient for delayed release of the inorganic nitrite, or pharmaceutically acceptable salt thereof, such that, when orally administered to a subject, the inorganic nitrite or pharmaceutically acceptable salt thereof is not substantially released in the stomach of the subject.

By "chronic pain" is meant pain that lasts longer than three to six months or pain that extend beyond the expected period of healing. Chronic pain may originate with an initial trauma/injury or infection, or may be an ongoing cause of pain associated with neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome), headaches, joint pain, backaches, sinus pain, muscle pain, nerve pain, and pain affecting specific parts of the body, such as shoulders, pelvis, and neck. Chronic pain may also be associated with lower back pain, arthritis, headache, multiple sclerosis, fibromyalgia, shingles, nerve damage, or cancer.

As used herein, the term "delayed release" refers to a pharmaceutical preparation, e.g., an orally administered formulation, which passes through the stomach substantially intact and dissolves in the small and/or large intestine (e.g., the colon). In some embodiments, delayed release of the active agent (e.g., nitrite as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably refer to a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" refer to pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approximately 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "pharmaceutical composition," as used herein, represents a composition containing a compound described herein (e.g., inorganic nitrite, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, means a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "reducing," as used herein, refers to treatment that alleviates one or more symptoms or conditions of a disease, disorder, or conditions described herein (e.g., pain). Treatment can be initiated, for example, following ("post-exposure prophylaxis") an event that precedes the onset of the disease, disorder, or conditions in a subject that has been predisposed or previously diagnosed with the disease and/or condition. Treatment that includes administration of a compound of the invention, or a pharmaceutical composition thereof, can be acute, short-term, or chronic. The doses administered may be varied during the course of the treatment.

By "improvement in mood or psychological state" is meant a positive change in a subject's emotional state.

By "modulates brain function" is meant to regulate or adjust the levels of NO in the brain such that there is homeostatic signaling occurring in the brain.

By "predisposition or is diagnosed" is meant a population of subjects (e.g. mammals, including humans and non-humans) that has been pre-selected as having a condition associated with pain, a mood disorder and/or an imbalance in psychological state, or a disorder of brain development. The conditions associated with pain include but is not limited to: musculo-skeletal pain (after trauma, infections), neuropathic pain caused by diabetes, infections, metabolic disorders, exposure to toxins, traumatic injury, spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative pain. Mood disorders include but are not limited to: major depressive disorders, depressive disorders, bipolar disorders, substance induced mood disorders, alcohol induced mood disorders, and benzodiazepine induced mood disorders. Disorders of brain development include but are not limited to: impairment in learning and memory, autistic disorder, Rett syndrome, childhood disintegrative disorder, pervasive developmental disorder-not otherwise specified (PDD-NOS), and Asperger syndrome.

The term "prodrug," as used herein, represents compounds which are rapidly transformed in vivo to the parent compound of the above formula. Prodrugs also encompass bioequivalent compounds that, when administered to a human, lead to the in vivo formation of nitrite ion ($NO_2^-$) or nitrous oxide (NO). A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable such as those described in EP 1336602A1, which is herein incorporated by reference.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, retarding or reversing the progress of, or alleviating either the disease or condition to which the term applies, or one or more symptoms of such disease or condition.

The term "unit dosage forms" refers to physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" refers to the amount of nitrite ion present in the plasma of a treated subject (e.g., as measured in a rabbit using an assay described below or in a human).

By "about" is meant ±20% of the recited value.

Other features and advantages of the invention will be apparent from the following Detailed Description, the drawings, and the claims.

BRIEF DESCRIPTION OF THE DRAWINGS

FIG. 1A shows results from the physical quality of life assessment in the placebo, 40 mg, and 80 mg group. FIG. 1B shows results from the psychological quality of life assessment in the placebo, 40 mg, and 80 mg group.

FIG. 2A shows results from the WIQ in the FAS population. FIG. 2B shows results from the WIQ in the diabetic population.

DETAILED DESCRIPTION

Figure 1A:
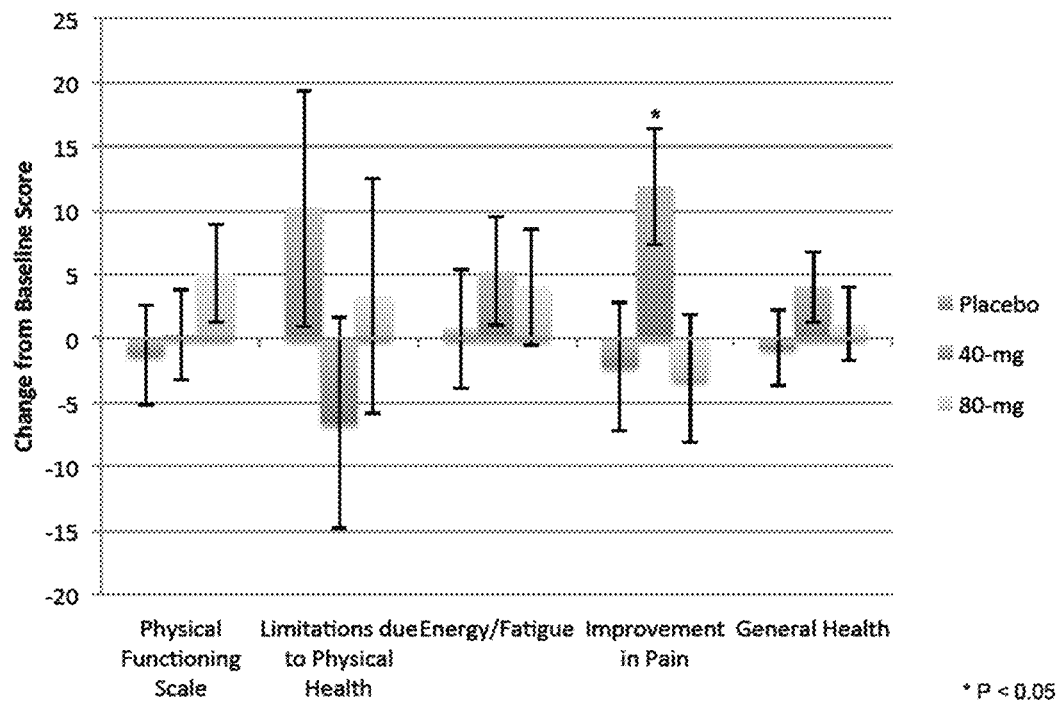
FIGS. 1A-1B show the results from the RAND 36 Questionnaire.

The invention features methods to treat and/or alleviate pain, particularly neuropathic pain (e.g., diabetic peripheral neuropathy, post-herpetic neuralgia, trigeminal neuralgia, phantom limb pain, carpal tunnel syndrome, sciatica, pudendal neuralgia, and central pain syndrome), modulate brain function, to improve mood and/or psychological state, and treat disorders of brain development, such as autism.

Nitrite

Inorganic Nitrite

The pharmaceutically acceptable compositions of the invention include inorganic nitrite, e.g., a salt or ester of nitrous acid ($HNO_2$), or a pharmaceutically acceptable salt thereof. Nitrite salts can include, without limitation, salts of alkali metals, e.g., sodium, potassium; salts of alkaline earth metals, e.g., calcium, magnesium, and barium; and salts of organic bases, e.g., amine bases and inorganic bases. Compounds of the invention also include all isotopes of atoms occurring in the intermediate or final compounds. Isotopes include those atoms having the same atomic number but different mass numbers. For example, isotopes of hydrogen include tritium and deuterium. The term "compound," as used herein with respect to any inorganic nitrite or pharmaceutically acceptable salt, solvate, or prodrug thereof. All compounds, and pharmaceutical acceptable salts thereof, are also meant to include solvated (e.g., hydrated) forms. Nitrite has the chemical formula $NO_2^-$ and may exist as an ion in water. Sodium nitrite has the chemical formula $NaNO_2$ and typically dissolves in water to form the sodium ion $Na^+$ and the nitrite ion $NO_2^-$. It will further be understood that the present invention encompasses all such solvated forms (e.g., hydrates) of the nitrite compounds. Exemplary nitrite compounds are described in WO 2008/105730, which is hereby incorporated by reference.

In addition to sodium nitrite, representative inorganic nitrite compounds include: ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II) nitrite ($Co(NO_2)_2$), cobalt(III) potassium nitrite ($CoK_3(NO_2)_6$; e.g., cobalt(III) potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), postassium nitrite ($KNO_2$), rubidium nitrite ($RbNO_2$), silver(I) nitrite ($AgNO_2$), strontium nitrite ($Sr(NO_2)_2$), and zinc nitrite ($Zn(NO_2)_2$).

The compounds of the present invention can be prepared in a variety of ways known to one of ordinary skill in the art of chemical synthesis. Methods for preparing nitrite salts are well known in the art and a wide range of precursors and nitrite salts are readily available commercially. Nitrites of the alkali and alkaline earth metals can be synthesized by reacting a mixture of nitrogen monoxide (NO) and nitrogen dioxide ($NO_2$) with a corresponding metal hydroxide solution, as well as through the thermal decomposition of the corresponding nitrate. Other nitrites are available through the reduction of the corresponding nitrates.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Suitable pharmaceutically acceptable salts include, for example, sodium nitrite, potassium nitrite, or calcium nitrite. Still other exemplary salts are found in Remington's Pharmaceutical Sciences, 17th ed., Mack Publishing Company, Easton, Pa., 1985, p. 1418, Berge et al., *J. Pharmaceutical Sciences* 66:1-19, 1977 and *Pharmaceutical Salts: Properties, Selection, and Use*, (Eds. P. H. Stahl and C. G. Wermuth), Wiley-VCH, 2008, each of which is incorporated herein by reference in its entirety.

Pharmaceutical Compositions

When employed as pharmaceuticals, inorganic nitrite, e.g., a salt of nitrous acid ($HNO_2$) such as $NaNO_2$, or a pharmaceutically acceptable salt, solvate, or prodrug thereof can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. In one embodiment, the inorganic nitrite is administered in a pharmaceutical composition taught in U.S. patent application Ser. No. 12/904,791, hereby incorporated by reference.

The pharmaceutical composition can contain one or more pharmaceutically acceptable carriers. In making a pharmaceutical composition for use in a method of the invention, the inorganic nitrite, pharmaceutically acceptable salt, solvate, or prodrug thereof is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

The pharmaceutical composition can include nitrate salts, or prodrugs thereof, or other therapeutic agents. Exemplary nitrate salts are described in WO 2008/105730. Exemplary therapeutic agents that may be included in the compositions described herein are provided herein.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg; from about 0.5 mg to about 20 mg, from about 0.5 mg to about 10 mg, from about 0.5 mg to about 5 mg; from about 1 mg from to about 50 mg, from about 1 mg to about 30 mg; from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 40 mg to about 80 mg of the active ingredient, or from about 50 mg to about 80 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, *acacia*, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Formulations for Colonic Drug Release

In some embodiments, colon-targeted drug delivery systems can be used. Exemplary approaches include, but are not limited to:

(a) covalent linkage of the drug with the carrier to form a prodrug that is stable in the stomach and small intestine and releases the drug in the large intestine upon enzymatic transformation by the intestinal microflora; examples of these prodrugs include azo-conjugates, cyclodextrin-conjugates, glycoside-conjugates, glucuronate conjugates, dextran-conjugates, polypeptide and polymeric conjugates;

(b) approaches to deliver intact molecule to the colon, such as coating with pH-sensitive polymers to release the drug at neutral to alkaline pH, or coating with biodegradable polymers which release the drug upon degradation by the bacteria in the colon;

(c) embedding the drug in biodegradable matrices and hydrogels which release the drug in response to the pH or biodegradation;

(d) time released systems where once the multicoated formulation passes the stomach, the drug is released after a lag time of 3-5 hrs which is equivalent to the transit time of the small intestine;

(e) using redox-sensitive polymers where a combination of azo and disulfide polymers, provide drug release in response to the redox potential of the colon;

(f) using bioadhesive polymers which selectively adhere to the colonic mucosa slowly releasing the drug; and (g) osmotic controlled drug delivery where the drug is released through semi-permeable membrane due to osmotic pressure.

Routes of Administration

The compositions described herein may be administered to a patient in a variety of forms depending on the selected route of administration, as will be understood by those skilled in the art and as relating to the particular disease or condition to be treated. The compositions used in the methods described herein may be administered, for example, by topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time.

For intravenous or intrathecal delivery or direct injection, the composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved. For example, for local effects, the composition can be formulated for topical administration and applied directly where its action is desired. For systemic, long term effects, the composition can be formulated for enteral administration and given via the digestive tract. For system, immediate and/or short term effects, the composition can be formulated for parenteral administration and given by routes other than through the digestive tract.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Dosing Regimes

The present methods for modulating brain function, in particular improving mood and/or psychological state, in the treatment of disorders of brain development, and in the treatment and/or reduction of pain are carried out by administering an inorganic nitrite for a time and in an amount sufficient to result in the improvement of mood and/or psychological state, in the treatment and/or reduction of pain, and in the treatment of disorders of brain development.

The amount and frequency of administration of the compositions can vary depending on, for example, what is being administered, the state of the patient, and the manner of administration. In therapeutic applications, compositions can be administered to a patient suffering from pain (e.g., neuropathic pain, neuropathy, diabetic peripheral neuropathy) in an amount sufficient to relieve or least partially relieve the symptoms of pain (e.g., discomfort, soreness, tightness, or stiffness) and its complications (e.g., fatigue, sleeplessness, weakened immune system, depression, anxiety, stress, irritability, or disability). The dosage is likely to depend on such variables as the type and extent of progression of the pain (e.g., as determined by the "Pain Ladder" guideline from the World Health Organization), the severity of the pain (e.g., acute, subacute, or chronic), the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of pain or slowing its progression.

The amount of inorganic nitrite per dose can vary. For example, a subject can receive from about 0.1 µg/kg to about 10,000 µg/kg. Generally, the nitrite is administered in an amount such that the peak plasma concentration ranges from 150 nM-250 µM. Exemplary dosage amounts can fall between about 0.1 to about 2000 µg/kg; about 0.5 to about 1000 µg/kg; about 0.5 to about 2000 µg/kg; about 100 to about 1500 µg/kg; about 0.5 µg/kg to about 500 µg/kg; about 0.5 µg/kg to about 250 µg/kg; about 0.5 µg/kg to about 100 µg/kg; about 0.5 µg/kg to about 50 µg/kg; about 100 to about 350 µg/kg; about 340 to about 750 µg/kg; or about 750 to about 1000 µg/kg. Exemplary dosages can be about 8.25 µg/kg, about 10 µg/kg, about 16.5 µg/kg, about 20 µg/kg, about 30 µg/kg, about 50 µg/kg, about 100 µg/kg, about 165 µg/kg, about 200 µg/kg, about 500 µg/kg, about 750 µg/kg, about 1000 µg/kg, about 1250 µg/kg, about 1500 µg/kg, about 1750 µg/kg, or about 2000 µg/kg. Exemplary peak plasma concentrations can range from 0.05-10 µM, 0.1-10 µM, 0.1-5.0 µM, or 0.1-1 µM. The peak plasma concentrations may be maintained for 2-14 hours, 4-14 hours, 6-14 hours, 6-12 hours, or 6-10 hours.

The frequency of treatment may also vary. The subject can be treated one or more times per day (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention for modulating brain function, in particular improving mood and/or psychological state, in the treatment of disorders of brain development, and in the treatment and/or reduction of pain.

Methods of Treatment

The present invention provides nutritional and pharmaceutical compositions of nitrite, e.g., inorganic nitrite, or a pharmaceutically acceptable prodrug thereof, for both prophylactic and therapeutic nutritional supplementation, specifically in maintaining a balance in psychological state and alleviating pain (e.g., chronic pain). Specifically, the present invention relates to novel compositions of nitrite, e.g., inorganic nitrite, or a pharmaceutically acceptable prodrug thereof, that can be used to treat patients with acute pain, subacute pain, or chronic pain (e.g., pain that lasts longer than three to six months or pain that extend beyond the expected period of healing, and/or pain that originates from an initial trauma/injury or infection, or pain that may be an ongoing cause associated with neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome, headaches, joint pain, backaches, sinus pain, muscle pain, nerve pain, and pain affecting specific parts of the body, such as shoulders, pelvis, and neck, and/or pain that is associated with lower back pain, arthritis, headache, multiple sclerosis, fibromyalgia, shingles, nerve damage, or cancer. The present invention also relates to novel compositions of nitrite, e.g., inorganic nitrite, or a pharmaceutically acceptable prodrug thereof, that can be used to treat patients with mood disorders and/or an imbalance in psychological state, and disorders of brain development.

Pain

Following the clinical trials described in the Examples below, it was observed that patients who were taking the compositions of the invention also reported a reduction in pain. Therefore, it was postulated that the compositions of the invention may be useful in the treatment or reduction of pain in general and neuropathic pain in preferred embodiments.

Neuropathic Pain

Neuropathic pain can take a variety of forms depending on its origin and can be characterized as acute, subacute, or chronic depending on the duration. Acute pain can last anywhere from a couple hours to less than 30 days. Subacute pain can last from one to six months and chronic pain is characterized as pain that lasts longer than three to six months or pain that extend beyond the expected period of healing. In neuropathic pain, the pain may be described as being peripheral neuropathic if the initiating injury occurs as a result of a complete or partial transection of a nerve or trauma to a nerve plexus. Peripheral neuropathy can result from traumatic injuries, infections, metabolic disorders, diabetes, and/or exposure to toxins. Alternatively, neuropathic pain is described as being central neuropathic following a lesion to the central nervous system, such as a spinal cord injury or a cerebrovascular accident. The methods of the invention include administration of the compositions described herein to treat neuropathic pain. Types of neuropathic pain include but are not limited to: diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, and central pain syndrome.

Neuropathy

The compositions described herein are useful for the treatment of neuropathy, in particular, diabetic peripheral neuropathy. Neuropathy can have many causes such as sustained injury or exposure to toxins or chronic diseases (e.g., Parkinson's multiple sclerosis, autoimmune diseases, and diabetes), with diabetes as the biggest risk factor. In diabetic patients, it typically takes many years for neuropathy to develop as nerve damages result over time due to prolonged exposure to the damaging effects of high blood glucose levels. The longer a subject has diabetes, the higher the risk of developing neuropathy. The compositions described herein can be administered prophylactically to a subject having diabetes to prevent or reduce the risk of developing diabetic peripheral neuropathy or therapeutically to treat diabetic peripheral neuropathy.

Without wishing to be bound by theory, the compositions of nitrite described herein may be especially beneficial to a diabetic subject through its indirect effect on the sorbitol-aldose reductase pathway, which is implicated in diabetic complications. In diabetic subjects with a high hyperglycemic state, the affinity for aldose reductase for glucose increases which leads to higher levels of sorbitol and lower NADPH. NADPH specifically acts to promote nitric oxide (NO) and glutathione production, which results in vasodilation. The oxidation of NADPH to NADP+ is also necessary to prevent reactive oxygen species from forming. The lower NADPH levels in diabetic subjects inhibit NO production and may alone lead to neuronal cell death and pain. Thus, the ability to replenish the NO supply would in some instances ameliorate symptoms of neuropathic pain in subjects with diabetes.

Inflammatory Pain

Inflammatory pain is a form of pain that is caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. The different types of pain may coexist or pain may be transformed from inflammatory to neuropathic during the natural course of the disease, as in post-herpetic neuralgia.

Nociceptive Pain

Nociceptive pain is the pain experienced in response to a noxious stimulus, such as a needle prick or during trauma or surgery. Nociceptive pain may be divided into superficial and deep, and deep pain into deep somatic and visceral. Superficial pain is initiated by activation of nociceptors in the skin or superficial tissues. Deep somatic pain is initiated by stimulation of nociceptors in ligaments, tendons, bones, blood vessels, fasciae and muscles, and is dull, aching, poorly-localized pain. Visceral pain originates in the viscera (organs). Visceral pain may be well-localized, but often it is extremely difficult to locate, and several visceral regions produce referred pain when damaged or inflamed, where the sensation is located in an area distant from the site of pathology or injury.

Other Types of Pain

Functional pain refers to conditions in which there is no obvious peripheral pathology or lesion to the nervous system. This particular form of pain is generated by abnormal function of the nervous system and conditions characterized by such pain include fibromyalgia, tension-type headache, and irritable bowel syndrome.

Common conditions associated with chronic pain include but are not limited to back injuries (e.g., slipped or bulging discs, spinal stenosis, compression fractures, soft tissue damage, traumatic fractures, and structural deformities), headaches (e.g., muscle tension headaches, eye strain headaches, migraines, cluster headaches), joint pain (e.g., osteoarthritis, rheumatoid arthritis, and repetitive strain injury), fibromyalgia, and pain associated with cancer (e.g., leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer).

The pharmaceutical compositions and methods described herein may be useful for the treatment, reduction, or prevention of various forms of pain, namely inflammatory pain, nociceptive pain, functional pain, and neuropathic pain, whether acute or chronic. Exemplary conditions that may be associated with pain include, for example, soft tissue, joint, bone inflammation and/or damage (e.g., acute trauma, osteoarthritis, or rheumatoid arthritis), myofascial pain syndromes (fibromylagia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

The present invention may also be useful for the treatment or reduction of musculo-skeletal pain (after trauma, infections, and exercise), neuropathic pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative pain.

Assessment of Efficacy

The compositions described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured. In particular, the assessment of pain upon administration of the compositions of the invention in diabetic peripheral neuropathy can be studied in animal models such as the streptozotocin-induced diabetic rats and mice, which serves as a model of peripheral neuropathy of type 1 diabetes (see, e.g., Tesch et al., *Nephrology*. 12(3):261-266, 2007), the leptin deficient (ob/ob) mouse model, which serves as a model of peripheral neuropathy of type 2 diabetes (see, e.g., Drel et al., *Diabetes*. 55(12):3335-3343, 2006), the nonobese diabetic (NOD) mouse model, spontaneously induced Ins2 Akita mouse model, Db/Db leptin receptor deficient mouse model, WBN/Kob spontaneous diabetic rat model, SDT fatty rat model, high fat diet C5BL/6J mouse model, and Rhesus monkey PDN model (see, e.g., Islam, *J Diabetes Res.* 2013: 149452, 2013).

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compositions described herein (Stein et al., *Pharmacol*. Biochem. Behav. (1988) 31: 445-451; Woolf et al., *Neurosci*. (1994) 62: 327-331). Additionally, various tests assess peripheral neuropathic pain using lesions of the peripheral nervous system. One such example is the "axotomy pain model" (Watson, *J. Physiol*. (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCI) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied peri-neurally), models of post-herpetic neuralgia using HSV infection, and compression models.

Chronic pain has been characterized as a disease affecting brain structure and function. Magnetic resonance imaging studies have shown abnormal anatomical and functional connectivity, even during rest involving areas related to the processing of pain. Persistent pain has also been shown to cause grey matter loss, reversible once the pain has resolved. Thus, measures of neuroplasticity can be used to assess the efficacy of the compositions described herein. Brain electroencephalogram (EEG) can be used to measure the changes in relative beta activity, alpha activity, and theta activity in subjects taking with the composition compared to subjects not taking the composition.

Neuropathy affects the motor fibers or the large sensory fibers and traditional tools such as electromyography and nerve conduction studies are useful for determining the efficacy of administration of the compositions described herein to a subject. Quantitative sensory testing can also be used to determine efficacy of treatment. Quantitative sensory testing involves the application of controlled mechanical, thermal, or chemical stimuli. Subjects report their perception of the stimulus and indicate the point at which it becomes painful, which allows an evaluation of the subject's sensory threshold for various types of stimuli. Other in vivo assays to measure effectiveness of the compositions include monofilament testing and nerve conduction velocity testing. Skin biopsies maybe also be useful for monitoring response to therapy or disease progression. Skin biopsies require a small sample of the epidermis be taken, using local anesthetic, from anywhere on the body. The biopsy sample is immunolabeled with an antibody against PGP9.5, a panaxonal marker so the small sensory nerve endings in the skin can be seen and counted using a light microscope. Skin biopsies allow quantitative measurement of the sensory nerve endings in the epidermis because they exist as individual nerve endings that can be counted. Normative data are available to show the normal density of cutaneous nerve endings and provide a point of comparison for the test subject. Other ex vivo efficacy testing include histopathology or biopsy of tissues to look for changes in axonal atrophy, axonal dystrophy in myelination (i.e., demyelination), and reduced numbers of large myelinated fibers.

In all of the above tests, outcome measures may be assessed, for example, according to behavior, electrophysiology, neurochemistry, or imaging techniques to detect changes in neural activity. In all of the above tests, an improvement in pain reduction can also be assessed by determining the pharmacological and non-pharmacological characteristics of pain such as pain intensity (as measure on a standardized pain scale), pattern (e.g., constant, intermittent), location, radiation, frequency, timing, and duration, impact on quality of life (sleep, function, appetite, and mood).

Mood Disorders and Imbalance of Psychological State

NO signaling in the brain can modulate a range of processes such as various forms of plasticity (long term potentiation and depression, LTP and LTD), regulating rhythmic activity, including gut motility, respiratory rhythm, circadian rhythms, locomotor, and thalamocortical oscillation. The compositions described herein are effective NO-donor compounds delivering NO to specific sites, therefore these compositions may also be useful in modulating brain function, in particular improving mood and/or psychological state, and in the treatment of mood disorders, by maintaining a balance in the levels of NO.

The term mood disorder refers to the underlying or longitudinal emotional state observed in a subject. Two groups of mood disorders are broadly recognized; the division is based on whether a manic or hypomanic episode has ever been present. Thus, there are depressive disorders, of which the best-known and most researched is major depressive disorder (MDD) and bipolar disorder (BD), characterized by intermittent episodes of mania or hypomania, usually interlaced with depressive episodes. There are also forms of depression of MDD and BD that are less severe and are known as dysthymic disorder (in relation to MDD) and cyclothymic disorder (in relation to BD).

Other types of depressive disorders include but are not limited to: atypical depression, melancholic depression, psychotic major depression, catatonic depression, postpartum depression, seasonal affective disorder, and depressive disorder not otherwise specified (DD-NOS). Bipolar disorders include: bipolar I, bipolar II, cyclothymia, and bipolar disorder not otherwise specified (BD-NOS). Mood disorders can also be classified as substance induced. These substance-induced mood disorders include: alcohol-induced mood disorders, bezodiazepine-induced mood disorders, and stimulant-induced mood disorders (e.g., amphetamine, methamphetamine, and cocaine)

Disorders of Brain Development

NO is also involved in learning and memory mechanism through mediation of specific forms of LTP. As such, the compositions described herein may also be useful in treating disorders of brain development such as: impairment in learning and memory, autistic disorder, Rett syndrome, childhood disintegrative disorder, pervasive developmental disorder-not otherwise specified (PDD-NOS), and Asperger syndrome. Autism is a disorder of neural development characterized by impaired social interaction and communication, and by restricted and repetitive behavior.

Autism affects information processing in the brain by altering how nerve cells and their synapses connect and organize. Austism is among one of the three recognized disorders in the autism spectrum (ASDs), the other two being Asperger syndrome, which lacks delays in cognitive development and language, and pervasive developmental disorder. As autism is caused by neurological dysfunctions, the compositions of the invention may also be useful in the treatment of autism and related neural development disorders.

Rett syndrome, originally termed as cerebroatrophic hyperammonemia, is a neurodevelopmental disorder of the grey matter of the brain that almost exclusively affects females but has also been found in male patients. The clinical features include small hands and feet and a deceleration of the rate of head growth (including microcephaly in some). Repetitive stereotyped hand movements, such as wringing and/or repeatedly putting hands into the mouth, are also common clinical features. Subjects with Rett syndrome are prone to gastrointestinal disorders and up to 80% have seizures and typically have no verbal skills. About 50% of individuals affected are not ambulatory. Scoliosis, growth failure, and constipation are very common features of Rett syndrome and can be problematic. Rett syndrome is listed under the broad category of pervasive developmental disorders.

Childhood disintegrative disorder (CDD), also known as Heller's syndrome and disintegrative psychosis, is a rare condition characterized by late onset (>3 years of age) of developmental delays in language, social function, and motor skills. CDD has some similarity to autism, and is sometimes considered a low-functioning form of it, but an apparent period of fairly normal development is often noted before a regression in skills or a series of regressions in skills. Many children are already somewhat delayed when the disorder becomes apparent, but these delays are not always obvious in young children. The age at which this regression can occur varies, and can be from age 2-10 with the definition of this onset depending largely on opinion. Some children describe or appear to be reacting to hallucinations, but the most obvious symptom is that skills apparently attained are lost.

Combination Therapy/Treatment

The compositions and methods of the invention can also be used in conjunction with other remedies known in the art that are used to treat pain, mood disorders and/or imbalances in psychological state, or disorders of brain development including non-steroidal anti-inflammatory drugs (NSAIDs), corticosteroids, acetaminophen, opioids, muscle relaxants, anti-anxiety drugs, anti-depressants, anti-convulsant drugs, antipsychotics, mood stabilizers, lithium, and serotonin reuptake inhibitors (SSRIs). The compositions and methods of the invention can also be used in conjunction with other forms of treatment including but not limited to: cognitive-behavioral therapies, music therapies, art therapies, group therapies, psychotherapies, physical exercise, pet therapies, communication therapies, educational therapies, and family therapies. The choice of specific treatment may vary and will depend upon the severity of the pain, mood disorder, or disorder of brain development, the subject's general health, and the judgment of the attending clinician.

For the treatment of neuropathic pain, the compositions of the invention can be used prior to, concurrently with, or subsequent to administration of tricyclic antidepressants (TCAs), such as amitriptyline, selective serotonin reuptake inhibitors (SSRIs) or norepinephrine inhibitors, such as duloxetine, milnacipran, and venlafaxine, antiepileptic drugs (AEDs), such as gabapentin, pregabalin, topiramate, and levetiracetam, and other neuropathic pain agents, such as nortriptyline, bupropion, desipramine, nonsteroidal anti-inflammatories, opioids (e.g., codeine, lydrocodone, hydromorphone, methadone, morphine, oxycodone), lidocaine, gallium maltolate, and cannabinoids.

The present compositions can also be formulated in combination with one or more additional active ingredients, which can include a pharmaceutical agent such NSAIDs (e.g., aspirin, ibuprofen, ketoprofen, ketorolac tromethamine, and naproxen), corticosteroids (e.g., prednisolone, methylprednisolone, hydrocortisone, amcinonide, fluocinonide, flunisolide, prednicarbate, betamethasone, and triamcinolone acetonide), acetaminophen, opioids (e.g., morphine, fentanyl, oxcodone, codeine), muscle relaxants (e.g., carisoprodol, cyclobenzaprine, and diazepam), anti-anxiety drugs (e.g., duloxetine, fluoxetine, alprazolam, escitalopram, and lorazepam), anti-depressants (e.g., desipramine, amitriptyline, agomelatine, etoperidone, and phenelzine), anti-convulsant drugs (e.g., lithium carbonate, lithium citrate, topiramate, oxcarbazepine, and valproic acid), antipsychotics (e.g., aripiprazole, clozapine, risperidone, asenaphine, and olanzapine), and SSRIs (e.g., citalopram, paroxetine, fluvoxamine, and sertraline).

In one embodiment, any of the foregoing compounds may be formulation with an inorganic nitrite (e.g., sodium nitrite) or administered along with an inorganic nitrite (e.g., sodium nitrite) to a patient suffering from pain (e.g., diabetic neuropathy or another neuropathic pain). When co-administered, the two compounds are desirably administered within 24 hours of each other (e.g., within 12 hours, 8 hours, 4, hours, 2 hours, 1 hour, 30 minutes, 15 minutes, or substantially simultaneously).

In some embodiments, the composition also includes an inorganic nitrate; in other embodiments, the composition excludes inorganic nitrates. For example, the present composition can include inorganic nitrite and nitrates in a ratio that is between 1-5 to 1-100 nitrite:nitrate, e.g., 1-5, 1-10, 1-30, 1-50, 1-70, or 1-100 nitrite:nitrate.

EXAMPLES

The following list of abbreviations and definitions of terms are used in the examples described hereafter.

| Abbreviations | Term |
|---|---|
| ABI | Ankle Brachial Index |
| ACS | Acute Coronary Syndrome |
| AUC | Area Under Curve |
| AE | Adverse Event |
| BID | Twice Daily |
| CBC | Complete Blood Count |
| CFR | Code of Federal Regulations |
| CHF | Congestive Heart Failure |
| CNS | Central Nervous System |
| $C_{max}$ | Maximum Plasma Drug Concentration |
| $C_{tau}$ | Average Drug Concentration over Dosing Interval |
| DBP | Diastolic Blood Pressure |
| DLT | Dose-Limiting Toxicity |
| ECG | Electrocardiogram |
| eCRF | Electronic Case Report Form |
| EDC | Electronic Data Capture |
| FDA | Food and Drug Administration |
| FMD | Flow-Mediated Vasodilation |
| G6PD | Glucose-6 Phosphate Dehydrogenase |
| HbA1c | Hemoglobin A1c |
| ICF | Informed Consent Form |
| IL-6 | Interleukin-6 |
| IP | Investigational Product |
| LOCF | Last Observation Carried Forward |
| MDRD | Modification of Diet in Renal Disease Study |
| MetHb | Methemoglobin |
| NO | Nitric Oxide |
| NYHA | New York Heart Association |

-continued

| Abbreviations | Term |
|---|---|
| PAD | Peripheral Artery Disease |
| PD | Pharmacodynamic |
| PI | Principal Investigator |
| PK | Pharmacokinetic |
| QoL | Quality of Life |
| RAND 36 | RAND 36-Item Short Form Health Survey |
| SAE | Serious Adverse Event |
| SBP | Systolic Blood Pressure |
| SD | Standard Deviation |
| SICAM | Soluble Intercellular Adhesion Molecule |
| SOC | System Organ Class |
| TIA | Transient Ischemic Attack |
| VCAM | Vascular cell adhesion protein |
| WIQ | Walking Impairment Questionnaire |

Example 1

Phase 2a Clinical Studies

Study Rationale and Details

Sodium nitrite was investigated as a new therapy for improving function in subjects with PAD. The overall goal of this dose-ranging study was to evaluate the safety, pharmacokinetics, tolerability, and potential biological activity of multiple doses of oral sodium nitrite in subjects with PAD. As described in detail above, the primary pathophysiology of PAD is related to the limitation in blood flow of the lower extremities, resulting in limited exercise tolerance and decreased quality of life. A common feature of PAD is endothelial dysfunction, decreased NO bioavailability, and depletion of NO stores, a finding that may be compounded when PAD and metabolic diseases, such as diabetes, coexist. Sodium nitrite is an inorganic salt that is found and metabolized in vivo. At physiological concentrations, sodium nitrite is known to cause vasodilation.

The primary objective of this early stage clinical study was to evaluate the safety and tolerability of multiple doses of twice daily 40 mg and 80 mg sodium nitrite compared with placebo over a 10 week treatment period. The secondary objective of this study was to evaluate the pharmacokinetics of sodium nitrite and to demonstrate the pharmacodynamic effect of sodium nitrite on measures of biologic activity and functional measures of walking distance and claudication symptoms. Finally, the relationship between doses, plasma concentration of sodium nitrite, and pharmacodynamic effects were characterized and evaluated. In this study, multiple assessments of biological activity and ambulatory function were made during standardized tests of arterial reactivity and claudication-limited exercise. The pharmacodynamic assessments included: brachial artery flow-mediated vasodilation (FMD), six-minute walk test, selected biomarkers of interest, quality of life questionnaires (WIQ & RAND 36).

The primary endpoints included: clinical safety and tolerability data including spontaneous AE reporting, ECGs, vital signs, nursing/physician observation, and clinical laboratory values. The secondary endpoints included flow-mediated vasodilation responses, maximal distance covered during a six-minute walk test, plasma pharmacokinetics (including but not limited to AUC, $C_{max}$, $C_{tau}$) of sodium nitrite and the relationship to the pharmacodynamic assessments performed in this study, and quality of life (WIQ & RAND 36). Furthermore, exploratory pharmacodynamic/biomarker endpoints included changes in markers of inflammation, oxidative stress, metabolic function, angiogenesis, or other markers of atherosclerotic disease, as data permitted (e.g. sodium nitrite, nitrite, nitrate, soluble intercellular adhesion molecule (SICAM), Vascular cell adhesion protein (VCAM), F2-isoprostanes and Interleukin-6 (IL-6)).

The trial type was a randomized, double-blind, placebo-controlled, dose ranging, parallel design multiple dosing study targeted on subjects with PAD. Subjects were at least 35 years of age, but not greater than 85 years of age. If the subject experienced claudication, the subjects also had a 1 month history of stable PAD symptoms. Subjects were assigned to either the placebo or sodium nitrite treatment group in accordance with the randomization schedule generated prior to the start of the study. Subjects were randomized into the study by means of an interactive web response system (IWRS) through electronic data capture (EDC) to receive one of the treatment regimens of either placebo, 40 mg BID or 80 mg BID. As this was a double-blind study, subjects, investigators, and site staff were blinded. TheraVasc and CPC were also blinded. In the case of a medical emergency or in the event of a serious medical condition, when knowledge of the investigational product was essential for the clinical management or welfare of the subject, an investigator or other physician managing the subject could unblind that subject's treatment code. The investigator made every effort to contact the CPC Medical Monitor before unblinding to discuss options. If the blind was broken for any reason and the investigator was unable to contact CPC prior to unblinding, the investigator must notify CPC as soon as possible following the unblinding incident without revealing the subject's study treatment assignment, unless the information was important to the safety of subjects remaining in the study. In addition, the investigator would record the date and reason for revealing the blinded treatment assignment for that subject in the appropriate data collection tool. If an expedited regulatory report to one or more regulatory agencies was required, the report identified the subject's treatment assignment. When applicable, a copy of the regulatory report was sent to investigators in accordance with relevant regulations, CPC policy, or both.

The Investigational Product (IP)

Capsules of sodium nitrite at dose strength of 40 mg and 80 mg per capsule which were to be stored at controlled room temperature (20-25° C., 68-77° F.). Matching placebo capsules were also supplied and stored at controlled room temperature. TV1001 was supplied in 50 count bottles dispensed in accordance with the visit schedule described in Table 1. IP was stored under secure conditions. Bilcare, Global Clinical Supplies labeled, stored and distributed the sodium nitrite and matching placebo. IP was assigned and administered as described below. Table 2 describes details of the study drug.

TABLE 1

Schedule of Assesments

| | Screening | Visit 1 Randomization | Visit 2 | Visit 3 | Safety Visit | Visit 4 | Visit 5 | Phone call 1 | Phone call 2 | Visit 6 | Visit 7 | Safety visit[1] | Termination visit | Follow-up phone call | Early term |
|---|---|---|---|---|---|---|---|---|---|---|---|---|---|---|---|
| Timing (days) | −21 to −14 days | Day 0 | Day 1 | Day 4 | Day 7 | Day 14 | Day 28 | Day 42 | Day 56 | Day 70 | Day 71 | Day 71 +1 | 6 Days after V7 | 7 Days after V8 or ET | n/a |
| Allowable variance | | | ±4 hours | ±1 day | ±1 day | ±2 day | ±2 day | ±2 day | ±2 day | ±2 day | ±1 day | ±1 day | ±1 day | ±1 day | |
| Informed consent | X | | | | | | | | | | | | | | |
| Demographics | X | | | | | | | | | | | | | | |
| Medical and Medication History | X | X | | | | | | | | | | | | | |
| Physical examination | X | | | | | | | | | | | | X | | X |
| Vital Signs[2] | X | X | X | X | X | X | X | | | X | X | X | X | | X |
| 12-Lead ECG | | X | | | | | X | | | | | | X | | X |
| Clinical safety labs | X | | X | X | | X | X | | | X | X | | X | | X |
| Met-Hb Labs[3] | | | X | X | X | X | X | | | X | X | X | X | | X |
| PK sample | | | X | X | | X | X | | | X | X | | X | | X |
| PK and Met-Hb over 7 time points[3] | | X | | | | | | | | | | | | | |
| Urine pregnancy test | X | X | | | X | | | | | | | | X | | X |
| PD Biomarkers | | X | | | | | | | | X | | | | | X |
| Ankle Brachial Index (ABI) | X | | | | | | | | | | | | | | |
| FMD[4] | | X | | | | | | | | X | | | | | X |
| QoL (WIQ, RAND36) | | X | | | | | | | | X | | | | | X |
| Six-Minute Walk Test | | X | | | | | | | | X | | | | | X |
| Study Medication Dispensed | | X | | | | X | X | | | X | | | | | X |
| Adverse Events | | X | X | X | X | X | X | X | X | X | X | X | X | X | X |
| Concomitant Medication | | X | X | X | X | X | X | X | X | X | X | X | X | X | X |

TABLE 1-continued

Schedule of Assesments

| | Screening | Visit 1 Randomization | Visit 2 | Visit 3 | Safety Visit | Visit 4 | Visit 5 | Phone call 1 | Phone call 2 | Visit 6 | Visit 7 | Safety visit[1] | Termination visit | Follow-up phone call | Early term |
|---|---|---|---|---|---|---|---|---|---|---|---|---|---|---|---|
| Evaluate Inclusion/Exclusion Criteria | X | X | | | | | | | | | | | | | |
| Evaluate Study Stopping Criteria | | X | X | X | X | X | X | | | X | X | X | | | |

[1]This visit was only required if Met-Hb is 8% or greater.
[2]Vital signs are supine prior to first dose of IP and postural after first dose.
[3]Repeated blood draws occured at baseline (pre-dose) and post-dose at 15 minutes ± 5 minutes, 30 minutes ± 5 minutes, 1 hour ± 10 minutes, 2 hours ± 10 minutes, 4 hours ± 10 minutes, and 6 hours ± 10 minutes.
[4]FMD may be done 7 days prior to the rest of Visit 1 and 5 days prior to the rest of Visit 6.

TABLE 2

Study Drug

| Study Drug | TV1001 | Placebo |
|---|---|---|
| Form | Capsule | Capsule |
| Available Unit dose strength(s) | 40 and 80 mg | 40 and 80 mg matched |
| Route/Administration | Administer orally | Administered oraly |
| Supplier | TheraVasc Inc. | TheraVasc Inc. |
| Manufacturer | UPM Pharmaceuticals 6200 Seaforth Street, Baltimore, MD 21224 | UPM Pharmaceuticals 6200 Seaforth Street, Baltimore, MD 21224 |

Subjects were instructed to return unused study medication and empty packaging at each study visit; all returned capsules were counted and recorded on the appropriate form. Compliance was calculated as the number of capsules taken divided by the number of capsules expected. If a subject was taking fewer capsules than expected, the site staff would counsel the subject on the importance of IP compliance. Investigators were responsible for receipt and proper storage of study medication, as well as for maintaining records of product delivery to site, inventory at site, dispensing of product to each subject, and return of product to TheraVasc, or designee, at the end of the study. All used, unused and partially used medication packages were returned according to TheraVasc, or designee, instructions.

The study was stopped if there were significant changes in safety parameters or significant AEs considered to be related to treatment with study medication (i.e., an imbalance in the safety profile in subjects receiving active drug vs. placebo). An individual subject was withdrawn at the discretion of the responsible investigator and the site study team for the reasons listed below as well as for other safety reasons that may not be listed. In the event one or more subjects were withdrawn, additional subjects were enrolled to ensure an adequate number of subjects complete the cohort. Specific reasons for an individual subject to withdraw included but was not limited to:

Subjects with a pattern of severe adverse events in any SOC, or cardiac monitoring findings as determined by the investigator and/or the sponsor.

Subjects with methemoglobin value 15% on any one occasion during study participation.

Subjects with normal baseline blood pressure who experienced any of the following: an increase in blood pressure to 160 mm Hg systolic and/or 90 mmHg diastolic that persists over 24 hours, an increase from baseline blood pressure of 30 mm Hg systolic and/or 15 mm Hg diastolic that persists over 24 hours, any symptomatic increase in blood pressure.

Subjects with stable elevated blood pressure at baseline who experienced any of the following: an increase in blood pressure to 180 mm Hg systolic and/or 100 mmHg diastolic that persists over 24 hours, an increase from baseline blood pressure of 20 mm Hg systolic and/or 10 mm Hg diastolic that persists over 24 hours, any symptomatic increase in blood pressure.

Subjects who experienced a decrease from baseline blood pressure of 20 mm Hg systolic with or without an increase of 10 beats per minute (BPM) pulse and the presence of symptoms.

Any subject who developed hypertension or hypotension requiring intervention were followed to resolution, preferably until any intervention therapy was withdrawn.

There were no Data Monitoring Committee (DMC) in place for this study and safety was monitored by the designated Study Medical Expert. A Steering Committee was formed comprising the Sponsor's CEO, two clinicians with experience in clinical trials, a medical regulatory expert and a researcher with expertise in sodium nitrite and its biological effects. CPC provided monthly status reports to the Committee on subject recruitment at each site, monitored reports of the site activities, and other non-safety information regarding the trial. Similar reports were provided in a blinded manner by the distributor of the bottle kits relative to the number of kits distributed to each site, returned bottles, and any issues that arose in randomization or distribution of the IP, assuring that no information was provided to the Committee as to the actual randomization. The Committee would discuss the reports and if any protocol deviations or non-compliance to the investigator's agreement or general investigational plan were noted, action was promptly taken to correct such deviations and secure compliance or discontinue shipments of the investigational drug to the investigator, end the investigator's participation in the investigation, require that all investigational drug be returned to the sponsor, and notified to the FDA. The Committee monitored subject accrual at each site and when necessary discontinue sites that were failing to enroll subjects and add additional sites. The Committee met within two calendar days upon receiving any information that could affect subject safety. The Committee discussed all safety information with CPC, and reported to the FDA and all active clinical investigators any information relevant to the safety of the drug as required under 21 CFR 312.32. The committee made annual reports on the progress of the investigations in accordance with 21 CFR 312.33. No interim analysis was planned for this study.

Study Visits

The study visits included the following components:

Screening

This visit was conducted within 14 to 21 days of Visit 1—Randomization. A signed informed consent form (ICF) was obtained before any study-specific assessments were performed. The following screening assessments were performed: (1) Informed Consent, (2) Demographics, (3) Medical and Medication History, (4) Physical Exam, (5) Supine Vital Signs, (6) Clinical Safety Labs, (7) Urine Pregnancy Test, (8) Ankle Brachial Index, and (9) Evaluate Inclusion/Exclusion Criteria.

Visit 1-Randomization

This was considered Day 0 of the study. Subjects were randomized at this visit and given first dose of study medication. The following assessments were performed: (1) Update Medical and Medication History, (2) 12-Lead ECG, (3) Urine Pregnancy Test, (4) FMD (may be performed within 7 days prior to Visit 1), (5) Quality of Life Questionnaires (WIQ and RAND 36), (6) Six-Minute Walk Test, (7) Evaluate Inclusion/Exclusion Criteria, (8) Study Medication Dispensed (the dose of study medication occurred in clinic. Subjects remained on clinic site for safety follow-up until the last PK sampling was complete), (8) PK Sampling (pre-dose and post-dose: 15, 30 minutes±5 minutes, and 1, 2, 4, 6 hours±10 minutes), (9) MetHb Sampling (pre-dose and post-dose: 15, 30 minutes±5 minutes, and 1, 2, 4, 6 hours±10 minutes), (10) PD Biomarkers, (11) Postural Vital Signs, (12) Adverse Event/Concomitant Medication Assessment (adverse events were captured following administration of the first dose), and (13) Evaluate Study Stopping Criteria.

Visit 2 (Day 1)

This visit was conducted 1 day (24 hours)+/−4 hours following the time of first dose administration at Visit 1. The subject must have taken the morning dose of the study medication in clinic 30 minutes (+/−10 min) before PK sampling. The following assessments were performed: (1) Administration of morning dose of study medication, (2) Clinical Safety Labs, (3) PK Sampling, (4) MetHb Sampling, (4) Postural Vital Signs, (5) Adverse Event/Concomitant Medication Assessment, and (6) Evaluate Study Stopping Criteria Visit 3 (Day 4)

This visit was conducted 4+/−1 days following Visit 1. The subject must have taken the morning dose of the study medication in clinic 30 minutes (+/−10 min) before PK sampling. The following assessments were performed: (1) Administration of morning dose of study medication, (2) Clinical Safety Labs, (3) PK Sampling, (4) MetHb Sampling, (5) Postural Vital Signs, (6) Adverse Event/Concomitant Medication Assessment, (7) Evaluate Study Stopping Criteria (if the subject does not meet stopping criteria but does experience an increase in MetHb to 8% or higher, and optional safety visit at Day 7 was scheduled as described below).

Optional Safety Visit (Day 7)

This visit was conducted only if the subject had a MetHb at Visit 3 of 8% or higher. It should be conducted 7 days following Visit 1+/−1 day. The subject must have taken the morning dose of the study medication in clinic 30 minutes (+/−10 min) before MetHb sampling. The following assessments were performed: (1) Administration of morning dose of study medication, (2) MetHb Sampling, (3) Postural Vital Signs, (4) Adverse Event/Concomitant Medication Assessment, and (5) Evaluate Study Stopping Criteria Visit 4 (Day 14)

This visit was conducted 14+/−2 days following Visit 1. The subject must have taken the morning dose of the study medication in clinic 30 minutes (+/−10 min) before PK sampling. The following assessments were performed: (1) Administration of morning dose of study medication, (2) Clinical Safety Labs, (3) PK Sampling, (4) MetHb Sampling, (5) Urine Pregnancy Test, (6) Postural Vital Signs, (7) Adverse Event/Concomitant Medication Assessment, (8) Evaluate Study Stopping Criteria, (9) Study Medication Compliance, and (10) Study Medication Dispensed Visit 5 (Day 28)

This visit was conducted 28+/−2 days following Visit 1. The subject must have taken the morning dose of the study medication in clinic 30 minutes (+/−10 min) before PK sampling. The following assessments were performed: (1) Administration of morning dose of study medication, (2) Clinical Safety Labs, (3) PK Sampling, (4) MetHb Sampling, (5) Postural Vital Signs, (6) 12-Lead ECG, (7) Adverse Event/Concomitant Medication Assessment, (8) Evaluate Study Stopping Criteria, (9) Study Medication Compliance, and (10) Study Medication Dispensed Phone Call 1

A phone call was placed to the subject 42+/−2 days following Visit 1. The subject was questioned regarding any adverse events and changes to concomitant medications.

Phone Call 2

A phone call was placed to the subject 56+/−2 days following Visit 1. The subject was questioned regarding any adverse events and changes to concomitant medications.

Visit 6 (Day 70)

This visit was conducted 70+/−2 days following Visit 1. The subject must have taken the morning dose of the study medication in clinic 30 minutes (+/−10 min) before PK sampling. The following assessments were performed: (1) Administration of morning dose of study medication (2) Clinical Safety Labs, (3) PK Sampling, (4) MetHb Sampling, (5) PD Biomarkers, (5) Postural Vital Signs, (6) FMD (may be performed within 5 days prior to Visit 6), (7) Quality of Life Questionnaires (WIQ and RAND 36), (8) Six-Minute Walk Test, (9) Adverse Event/Concomitant Medication Assessment, (10) Evaluate Study Stopping Criteria, and (11) Study Medication Compliance.

Visit 7 (Day 71)

This visit was conducted 1 day+1 day following Visit 6. The subject must have taken the morning dose of the study medication (dose escalation) in clinic 30 minutes (+/−10 min) before PK sampling. The following assessments were performed: (1) Study Medication Dispensed, (2) Administration of morning dose of study medication (upon dispensing and administering study medication, subjects were instructed to increase from 1 capsule BID to 2 capsules BID as described. Subject remained in clinic for a 1½ hours post dose observation), (3) Clinical Safety Labs, (4) PK Sampling, (5) MetHb Sampling (subject remained in clinic until results were available), (6) Postural Vital Signs, (7) Adverse Event/Concomitant Medication Assessment, (8) Evaluate Study Stopping Criteria (if the subject did not meet stopping criteria but experienced an increase in MetHb to 8% or higher, a safety visit at Day 70+2 was scheduled as described below in Optional Safety Visit (Visit 7+1), (9) Safety Assessment (immediately prior to subject departure), (10) Evaluation of MetHb results, and (11) Seated Vitals—Pulse Rate and BP.

Optional Safety Visit (Visit 7+1)

This visit was conducted only if the subject has a MetHb at Visit 7 of 8% or higher. It was conducted 1+1 day following Visit 7. The subject must have taken the morning dose of the study medication in clinic 30 minutes (+/−10 min) before MetHb sampling. The following assessments were performed: (1) Administration of morning dose of study medication, (2) MetHb Sampling, (3) Postural Vital Signs, (4) Adverse Event/Concomitant Medication Assessment, and (5) Evaluate Study Stopping Criteria.

Visit 8—Termination (Visit 7+6)

This visit was conducted 6+/−1 days following Visit 7. The subject must have taken the morning dose of the study medication in clinic 30 minutes (+/−10 min) before PK sampling. This would be the final dose and study visit. The following assessments were performed: (1) Physical Exam, (2) Clinical Safety Labs, (3) PK Sampling, (4) MetHb Sampling, (5) Urine Pregnancy Test, (6) Postural Vital Signs, (7) 12-Lead ECG, (8) Adverse Event/Concomitant Medication Assessment, and (9) Study Medication Compliance Follow-Up Phone Call A phone call was placed to the subject 7+/−1 days following Visit 8. If this subject early terminates from the study, a phone call was placed to the subject 7 days following the ET visit+/−1 day. The subject was questioned regarding any adverse events and changes to concomitant medications.

Early Termination Visit (ET)

In the case that a subject must withdraw early from study participation for any reason prior to Visit 6, every effort was made to complete an early termination visit. The subject must have taken the morning dose of the study medication in clinic 30 minutes (+/−10 min) before PK sampling unless the subject was withdrawn for safety and should stop taking IP immediately. The following assessments were performed: (1) Administration of morning dose of study medication, if applicable, (2) Physical Exam, (3) Clinical Safety Labs, (4) PK Sampling, (5) MetHb Sampling, (6) PD Biomarkers, (7) Postural Vital Signs, (8) 12-Lead ECG, (9) FMD (may be performed within 5 days prior to ET Visit), (10) Quality of Life Questionnaires (WIQ and RAND 36), (11) Six-Minute Walk Test, (12) Urine Pregnancy Test, (13) Adverse Event/Concomitant Medication Assessment, and (14) Study Medication Compliance. Moreover, if early termination occurred after Visit 6 but before the appropriate visit window for Visit 8, all procedures required at Visit 8 were completed.

Selection and Withdrawal of Subjects

The inclusion criteria included subjects between the ages of 35 and 85 years. Subjects must be either male or females post-menopausal, sterilized or using suitable birth control. Suitable birth control must be total abstinence, male partner sterilization or double barrier method paired with using oral contraception, injectable progestogen, implants of levonorgestrel, estrogenic vaginal ring, percutaneous contraceptive patches, or intrauterine device (IUD). A history of peripheral artery disease (PAD) was confirmed by medical chart or an ankle brachial index at rest of 0.90. If subjects received a medical standard treatment for cardiac risk factors, subject must have been on a stable treatment for at least 1 month prior to Screening. If included in this regimen, treatments such as cilostazol, pentoxifylline, statins, or angiotensin converting enzymes (ACE)-inhibitors; supervised exercise rehabilitation training; participation in a formal smoking cessation program or prescription of medications for smoking cessation were not changed significantly in the last month and were not expected to change over the duration of the study. If subjects experienced claudication symptoms, subjects must have stable lower extremity symptoms for at least 1 month (e.g. no change in claudication symptoms) prior to Screening. Subjects were required to provide written informed consent and willingness as documented by a signed informed consent form.

The exclusion criteria included subjects with non-atherosclerotic PAD (e.g. Buerger's vasculitis), lower extremity surgical or percutaneous revascularization, evidence of graft failure or other peripheral vascular surgical procedure within the last 6 months prior to Screening, anticipated lower extremity revascularization within the treatment period, myocardial infarction, unstable angina, cerebrovascular accident or transient ischemic attack (TIA) within 3 months prior to Screening, poorly controlled diabetes (HgA1c>10.0), poorly controlled hypertension (systolic blood pressure (SBP)≥160 mmHg or diastolic blood pressure (DBP)≥100 mmHg) despite therapy, systolic blood pressure≤100 mmHg on current medical regimen, hypersensitivity to sodium nitrite or related compounds, and renal insufficiency documented as eGFR<30 mL/minute/1.73 m$^2$ (Modification of Diet in Renal Disease Study MDRD). Exclusion criteria also included subjects who were pregnant or nursing women, who had a life expectancy of <6 months, a chronic illness that may increase the risks associated with this study in the opinion of the investigator, an active malignancy requiring active anti-neoplastic therapy that, in the opinion of the investigator, interfered with study treatment or participation (although stable basal cell skin cancer was allowed and cancer being treated solely with hormonal therapy was allowed), an active infection (i.e. systemic or osteomyelitis), a NYHA CHF Class III or IV, has had recent hospitalization (<30 days) for acute coronary syndrome (ACS), myocardial infarction (MI), congestive heart failure (CHF) or stroke, recent (<30 days) coronary revascularization had previously been treated with angiogenic factors or stem cell therapy within 1 year prior to Screening, was involved in another PAD clinical trial within past 1 month prior to Screening, had exposed tendon, muscle or bone or a diagnosis of critical leg ischemia (CLI), was previously amputated within 3 months prior to Screening, or had a planned amputation that would limit walking (although small toe is allowed). Exclusion criteria also included subjects whose ability to perform the 6 minute walk test was limited by symptoms other than claudication, who was diagnosed with alcohol or other substance abuse, had a history of methemoglobinema, (metHb 15%), who had an inability to speak English (due to need for administering standardized English-language questionnaire), who had evidence of anemia or a history of chronic hemolytic condition, including sickle cell disease, who had chronic use of anti-migraine medication such as Imitrex or sumatriptan, and a positive screen for glucose-6-phosphate dehydrogenase (G6PD) deficiency at screening. Subjects who chronically took the following medications: Allopurinol, PDE-5 inhibitors, sedative tricyclic antidepressants, sedative antihistamines, meperidine and related narcotic central nervous system (CNS) depressants, and nitrates were also excluded.

The withdrawal criteria allowed a subject to withdraw from the study at any time at his/her own request. The subject may also have been withdrawn at the Investigator's request if it was the Investigator's opinion that it was not in the subject's best interest to continue in the study. The subject was withdrawn if he or she met stopping criteria described above. In the event a subject was withdrawn from the study for any reason, the subject was followed-up with reasonable effort made to determine the reason for their withdrawal from the study and an ET visit as described above. Telephone calls, certified letters and offers of transportation assistance were considered reasonable effort. A summary of subject withdrawals is provided in Table 3.

TABLE 3

Subject Withdrawals
SUMMARY OF SUBJECT DISPOSITION

|  | Placebo n = 18 | 40 mg n = 19 | 80 mg n = 18 |
| --- | --- | --- | --- |
| Subjects who completed the study | 15 (83.3%) | 17 (89.5%) | 15 (83.3%) |
| Subjects who withdrew prior to completion | 3 (16.7%) | 2 (10.5%) | 3 (16.7%) |
| Reasons for withdrawal: |  |  |  |
| Adverse Event | 0 (0.0%) | 1 (5.3%) | 2 (11.1%) |
| Met withdrawal-new hypotension | 1 (5.6%) | 0 (0.0%) | 1 (5.6%) |
| Subject Request-lack of energy | 0 (0.0%) | 1 (5.3%) | 0 (0.0%) |
| Subject request-refused to continue | 1 (5.6%) | 0 (0.0%) | 0 (0.0%) |
| Subject request- no benefit | 1 (5.6%) | 0 (0.0%) | 0 (0.0%) |

Treatment of Subjects

Figure 3:
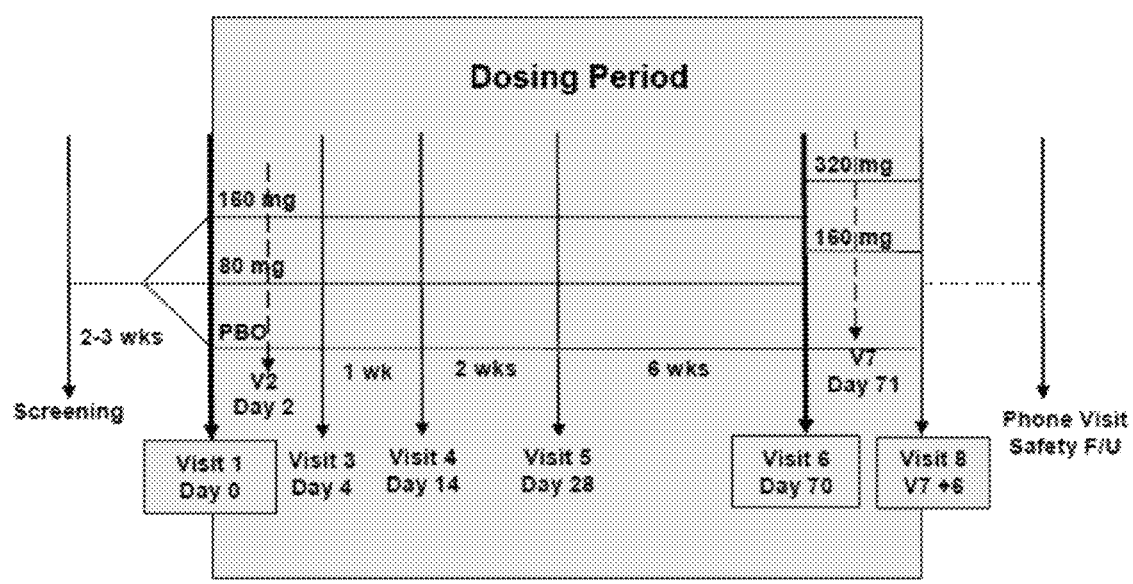
FIG. 3 is a flow chart showing the dosing arms for treatment of subjects.

The three dosing arms were placebo, 40 mg BID and 80 mg BID sodium nitrite as shown in FIG. 3. All doses were given as a twice-daily oral dose for 10 weeks. On the day following the 10 week dosing period and completion of efficacy assessments, subjects in each treatment arm entered a 6 day dose-escalation period (dose-doubling). Subjects in the 40 mg sodium nitrite BID group were dose-escalated to 80 mg sodium nitrite BID for 6 days, and subjects in the 80 mg sodium nitrite BID were dose-escalated to 160 mg sodium nitrite BID for 6-days. Placebo subjects doubled the number of placebo capsules taken BID. All study medication was stopped at the end of the 6-day dose-escalation period.

Subjects chronically taking Imitrex (sumatriptan), allopurinol, PDE-5 inhibitors, sedative tricyclic antidepressants, sedative antihistamines, meperidine and related narcotic CNS depressants, and nitrates were prohibited from participating in this study.

Subjects were instructed to return unused study medication at each study visit; all returned capsules were counted and recorded on the appropriate form. Compliance was calculated as the number of capsules taken divided by the number of capsules expected. The number of capsules taken was calculated by subtracting the number of capsules left from 50, the number of capsules in the bottle. If a subject took fewer capsules than expected, the site staff counseled the subject on the importance of IP compliance. Investigators were responsible for receipt and proper storage of study medication, as well as for maintaining records of product delivery to site, inventory at site, dispensing of product to each subject, and return of product to TheraVasc, or designee, at the end of the study. All used, unused, and partially used medication packages were returned according to TheraVasc, or designee, instructions.

Assessment of Efficacy

The efficacy parameters included: (1) flow-mediated vasodilation (FMD), six-minute walk test, pharmacokinetics (PK), biomarkers/pharmacodynamic (PD) markers, and quality of life (QoL) questionnaires.

Figure 1B:
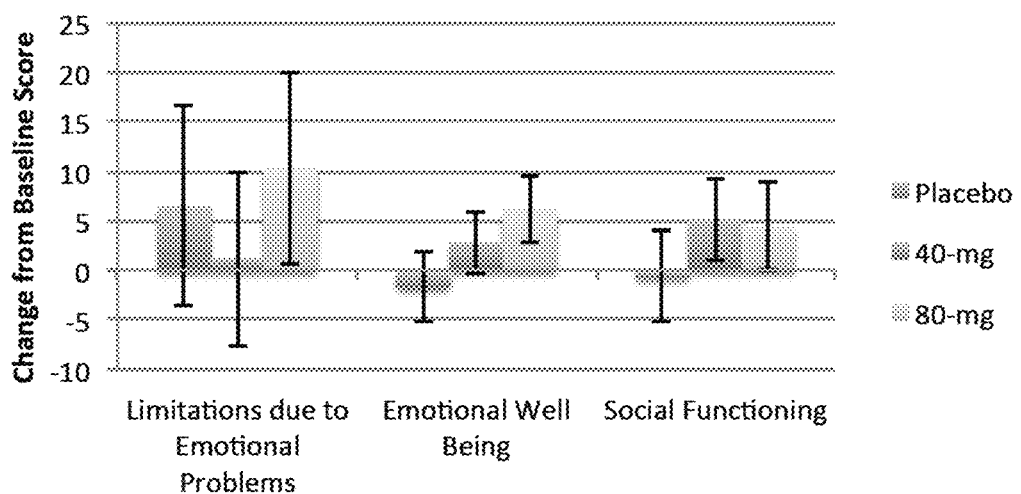
Figure 2A:
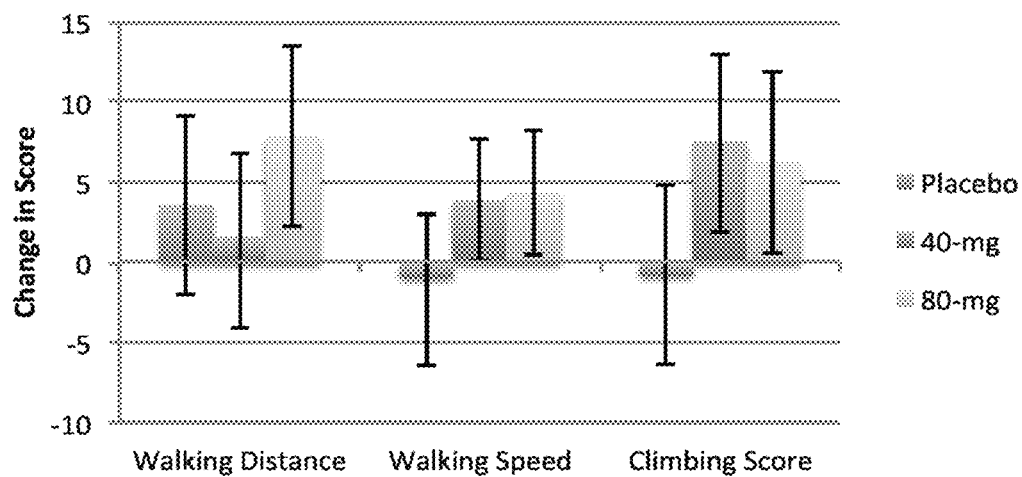
FIGS. 2A-2B show the results from the WIQ.
Figure 2B:
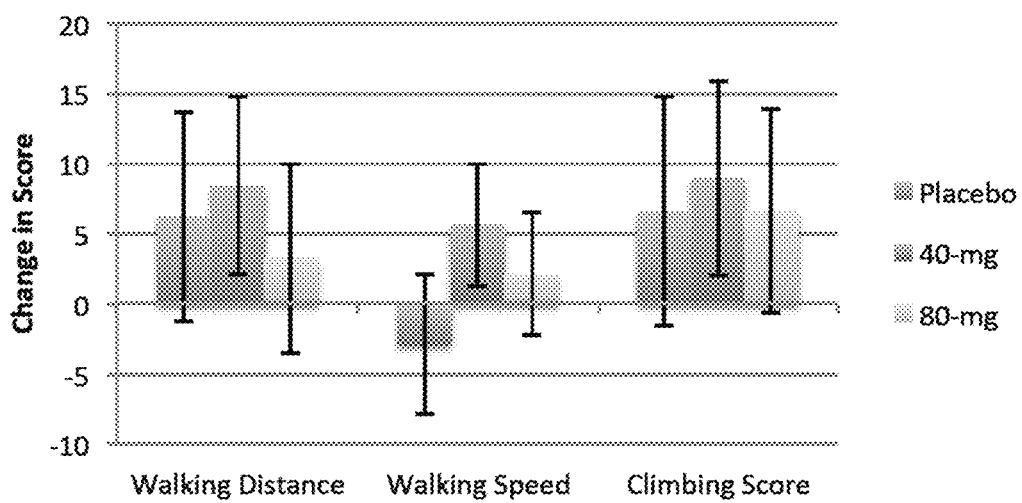

Of significance to the present invention are the responses relating to quality of life. Quality of life was measured by two questionnaires: WIQ and RAND 36. The two questionnaires were administered in the same sequence: WIQ first, followed by the RAND 36. The WIQ was a disease-specific instrument that measures community-based walking. The questionnaire consisted of four subscales (pain severity, distance, speed, and stairs). The WIQ was verbally administered to the subject by the Investigator, or designee. The RAND 36 was an instrument that measured general health issues. Study staff directed subjects to complete the RAND 36 on their own. Staff did not try to interpret the questions for the subject. If the subject did not understand a particular question, the study staff instructed the subject to interpret the meaning of the question to the best of his or her ability and provide an answer that seems most accurate to the subject. No family members or other individuals were allowed to answer questions or complete the questionnaire for the subject. All questionnaires were completed directly on the written source document pages. The study coordinator reviewed all questionnaires to ensure that there was only one response to each question, each question has been answered and any necessary corrections have been initialed and dated by the Investigator (or designee) or subject, accordingly. The results from the RAND 36 physical and psychological assessments are detailed in FIGS. 1A-B. RAND 36 showed a trend toward improvement in quality of life assessment and significant improvement in pain assessment in the 40 mg group. Results from the WIQ assessments are detailed in FIGS. 2A-B. WIQ showed no change in assessment in walking distance and a trend toward improvement in walking speed and stair climbing.

Assessment of Safety

The following safety parameters were assessed: medical and medication history, concomitant medication usage, physical examination, vital signs, 12-lead ECG, clinical chemistries, CBC, urinalysis, and adverse events. Urine pregnancy testing was completed for women of child-bearing potential who have not been surgically sterilized. Assessment of acute adverse events (i.e., drop in blood pressure, dizziness) was performed after administration of $1^{st}$ dose for each dose level of sodium nitrite. Dose-limiting toxicity (DLT) was defined as Grade 3 and clinically significant hematological events, particularly MetHb.

Overall, no severe adverse effects were observed in treated groups. Dose dependent hypotensive affects were observed demonstrating the hemodynamic affects of the treatment. Moreover, Methemoglobin levels were of no concern, even at the 160 mg dose escalation.

Demographic information (Table 4) and a complete medical history (Table 5) were obtained at the Screening Visit. Medical history for any ongoing ailments and for 5 years prior to screening and medication history for the past 1 month were documented. Medical and medication history was reviewed with the subject prior to randomization to ensure all data were accurate and complete to date.

TABLE 4

Demographic Data

| | | Placebo n = 18 | 40-mg n = 19 | 80-mg n = 18 |
|---|---|---|---|---|
| Age at informed consent (years) | | 64.9 +/− 8.98 | 65.3 +/− 8.86 | 67.9 +/− 9.99 |
| Gender | Male | 13 (72.2%) | 15 (78.9%) | 13 (72.2%) |
| | Female | 5 (27.8%) | 4 (21.1%) | 5 (27.7%) |
| Race/Ethnicity | Black or African American | 5 (27.8%) | 6 (31.6%) | 8 (44.4%) |
| | White | 12 (66.7%) | 12 (63.2%) | 10 (55.6%) |
| | Other | 1 (5.6%) | 1 (5.3%) | 0 (0.0%) |
| Weight(kg) | | 88.07 +/− 27.24 | 79.32 +/− 13.53 | 88.99 +/− 16.70 |
| Height(cm) | | 173.18 +/− 13.29 | 172.01 +/− 9.87 | 172.18 +/− 9.95 |
| Screening BMI (kg/m2) | | 29.32 +/− 8.31 | 26.71 +/− 2.99 | 30.01 +/− 5.03 |
| ABI in index limb at screening | | 0.56 +/− 0.15 | 0.62 +/− 0.20 | 0.69 +/− 0.17 |
| Diabetes Diagnosis | | 10 (55.6%) | 14 (73.7%) | 14 (77.8%) |
| Hb A1c (% Hb) at screening | | 6.97 +/− 1.48 | 6.99 +/− 1.27 | 6.71 +/− 0.94 |

TABLE 5

Medical History Background

| | Placebo N = 18 | 40-mg N = 19 | 80-mg N = 18 |
|---|---|---|---|
| PAD in last 5 years | 18(100%) | 19(100%) | 18(100%) |
| Peripheral revascularization in last 5 years | 8(44.4%) | 2(10.5%) | 8(44.4%) |
| Coronary artery disease in last 5 years | 6(33.3%) | 5(26.3%) | 7(38.9%) |
| Angina | 2(11.1%) | 0 | 4(22.2%) |
| Myocardial infarction | 0 | 2(10.5%) | 2(11.1%) |
| Coronary revascularization in last 5 years | 1(5.6%) | 0 | 4(22.2%) |
| Congestive Heart Failure | 1(5.6%) | 0 | 1(5.6%) |
| Cerebrovascular disease in last 5 years | 2(11.1%) | 3(15.8%) | 5(27.8%) |
| Ischemic stroke | 0 | 1(5.3%) | 1(5.6%) |
| TIA.mini-stroke | 1(5.6%) | 0 | 1(5.6%) |
| Hypertension | 16(88.9%) | 18(94.7%) | 16(88.9%) |
| Dyslipidemia | 15(83.3%) | 18(94.7%) | 16(88.9%) |
| Diabetes type 1 | 0 | 1(5.3%) | 0 |
| Diabetes type 2 | 10(55.6%) | 12(63.2%) | 12(66.7%) |
| Deep vein thrombosis/Pulmonary Embolism | 0 | 0 | 2(11.1%) |
| Stent/Balloon/Bypass | 5(27.8%) | 0 | 1 (5.6%) |

ABI assessments were measured at the screening visit in order to assess if the subject was appropriate according to inclusion criteria. ABI assessments were done only after the subject had been resting in a supine position for at least 10 minutes. The ABI was defined as the ratio between the higher of the two pedal systolic blood pressures (dorsalis pedis and posterior tibialis) and the higher of the two systolic brachial pressures. A continuous wave Doppler, between 5 and 10 MHz, was used to measure the systolic pressures in both the dorsalis pedis and posterior tibial arteries in each leg, as well as the brachial arteries in each arm. The higher of the 2 arm pressures and the higher of the 2 ankle pressures for each leg were used for the calculation. The ABI was calculated for both legs. The ABI must be less than 0.90 in at least one extremity to qualify for the study.

Site staff recorded any medication taken by a subject after randomization into the study, including prescribed, nutritional supplements and over-the-counter medications, and the reason for its use as a concomitant medication. If a subject required treatment by any medications listed as a prohibited concomitant therapy, he or she would be withdrawn from study participation and completed an ET visit.

A complete physical examination was performed at Screening and included height, weight and assessments of the following systems: general appearance; eyes; ears, nose, and throat; head and neck; chest and lungs; cardiovascular; abdomen; musculoskeletal; lymphatic; dermatological; neurological; and extremities. At Visit 8 or Early Termination a follow-up physical exam assessed weight and any changes to the above mentioned systems. Any significant changes noted at Visit 8 was documented as an adverse event unless otherwise noted by the PI or designee.

Supine vital signs were measured at the Screening Visit. The subject rested in a supine position for a minimum of 3 minutes prior to obtaining vital sign measurements. Vital signs included BP and pulse rate. Postural vital signs, including both supine and standing measurements of blood pressure and pulse rate, were recorded at all study visits following the first dose of IP administration. Measurements were performed as follows: (1) the subject rested in a supine position for a minimum of 3 minutes, (2) vital signs (BP and pulse rate) were measured while the subject was supine, (3) the subject assumed a standing position for a minimum of 5 minutes, and (4) vital signs (BP and pulse rate) were measured while the subject was standing. Pulse rate and blood pressure data are detailed in Table 6.

TABLE 6

Pulse Rate and Blood Pressure

| | | Screening | Visit 1 | Visit 2 | Visit 3 | Visit 4 | Visit 5 | Visit 6 | Visit 7 | Visit 8 |
|---|---|---|---|---|---|---|---|---|---|---|
| | | | | | Supine (Mean) | | | | | |
| Pulse | Placebo | 73.6 | 74.4 | 73.0 | 71.0 | 74.8 | 74.6 | 73.1 | 73.1 | 75.6 |
| | 40-mg | 71.4 | 74.1 | 74.1 | 74.7 | 71.7 | 72.7 | 7034 | 73.1 | 70.2 |
| | 80-mg | 63.9 | 65.6 | 65.1 | 66.7 | 64.6 | 68.7 | 65.5 | 64.3 | 68.3 |
| Blood Pressure | Placebo | 141.3/77.9 | 141.4/78.3 | 139.9/78.4 | 138.4/77.4 | 137.8/75.4 | 140.3/76.9 | 145.4/79.5 | 139.8/77.8 | 136.1/75.1 |
| | 40-mg | 136.8/75.8 | 129.7/72.3 | 128.0/70.5 | 129.3/72.5 | 128.4/71.1 | 124.1/72.0 | 127.3/73.7 | 126.7/71.3 | 130.0/72.2 |
| | 80-mg | 132.4/69.4 | 129.8/68.4 | 122.8/66.7 | 127.1/66.7 | 125.1/65.2 | 124.6/68.9 | 123.1/66.2 | 118.4/64.4 | 120.7/66.9 |

TABLE 6-continued

Pulse Rate and Blood Pressure

|  |  | Screening | Visit 1 | Visit 2 | Visit 3 | Visit 4 | Visit 5 | Visit 6 | Visit 7 | Visit 8 |
|---|---|---|---|---|---|---|---|---|---|---|
| Standing (Mean) | | | | | | | | | | |
| Pulse | Placebo | | 78.1 | 77.8 | 74.9 | 78.1 | 78.5 | 76.0 | 76.1 | 77.4 |
|  | 40-mg | | 75.8 | 78.6 | 76.7 | 75.6 | 76.6 | 73.9 | 76.3 | 74.3 |
|  | 80-mg | | 72.6 | 72.3 | 72.9 | 72.6 | 72.5 | 67.6 | 70.4 | 72.6 |
| Blood Pressure | Placebo | | 141.6/81.7 | 144.3/81.2 | 139.9/79.4 | 139.9/80.3 | 137.7/79.4 | 143.3/78.4 | 141.3/78.7 | 138.2/75.0 |
|  | 40-mg | | 129.5/73.1 | 128.3/72.6 | 129.4/73.1 | 124.9/71.0 | 124.3/71.6 | 127.6/73.2 | 122.2/73.2 | 123.1/68.7 |
|  | 80-mg | | 125.4/70.2 | 123.1/71.9 | 124.8/69.2 | 123.7/68.8 | 119.5/71.9 | 124.8/70.0 | 123.3/67.1 | 117.7/67.9 |
| Orthostatic Changes | | | | | | | | | | |
| Pulse | Placebo | | 3.7 | 4.8 | 3.9 | 3.3 | 3.9 | 2.9 | 3.0 | 1.8 |
|  | 40-mg | | 1.8 | 4.5 | 2.0 | 3.9 | 3.8 | 3.5 | 3.2 | 4.1 |
|  | 80-mg | | 6.9 | 7.3 | 6.2 | 7.9 | 3.8 | 2.1 | 6.1 | 4.3 |
| Systolic BP | Placebo | | 0.2 | 4.3 | 1.6 | 2.1 | −2.6 | −2.1 | 1.5 | 2.2 |
|  | 40-mg | | −0.3 | 0.3 | −0.4 | −3.4 | 0.3 | 0.3 | −4.5 | −6.9 |
|  | 80-mg | | −4.4 | 0.3 | −2.3 | −1.4 | −5.2 | 1.6 | 4.8 | −3.0 |
| Diastolic BP | Placebo | | 3.3 | 2.8 | 1.9 | 4.9 | 2.5 | −1.1 | 0.9 | −0.1 |
|  | 40-mg | | 0.8 | 2.1 | 0.6 | −0.1 | −0.4 | −0.5 | 1.9 | −3.5 |
|  | 80-mg | | 1.8 | 5.2 | 2.5 | 3.5 | 3.0 | 3.8 | 2.7 | 1.0 |

A resting 12-lead ECG printout with the subject in supine position was obtained at the time points listed in Table 1-Schedule of Assessments. All ECGs were assessed by the PI or qualified designee for clinical significance of any abnormalities or changes and documented on the ECG source document. Any clinically significant abnormalities that occured after the first dose of sodium nitrite was recorded as AEs on the eCRF. The 12-lead ECG was obtained immediately following vitals, with the exception of the Visit 1 Randomization day ECG which was collected prior to dosing. The ECG data details are provided in Table 7.

TABLE 7

ECG

|  | Visit 1 | Visit 5 | Visit 8 |
|---|---|---|---|
| Heart Rate (beats/minute) | | | |
| Placebo | 72.1 +/− 13.9 | 71.7 +/− 15.1 | 73.0 +/− 12.2 |
| 40-mg | 71.4 +/− 12.7 | 72.2 +/− 14.8 | |
| 80-mg | 62.7 +/− 10.7 | 65.5 +/− 11.9 | 74.3 +/− 10.0 |
| 160-mg | | | 64.7 +/− 10.0 |
| QTcB interval (msec) | | | |
| Placebo | 433.2 +/− 33.0 | 430.9 +/− 24.0 | 438.6 +/− 35.3 |
| 40-mg | 415.9 +/− 49.0 | 430.1 +/− 34.8 | |
| 80-mg | 422.3 +/− 34.0 | 411.6 +/−49.7 | 423.2 +/− 4.03 |
| 160-mg | | | 427.7 +/− 31.9 |
| QTcF interval (msec) | | | |
| Placebo | 421.2 +/− 31.4 | 419.7 +/− 22.5 | 425.4 +/− 33.9 |
| 40-mg | 404.8 +/− 44.9 | 417.7 +/− 24.0 | |
| 80-mg | 419.9 +/− 30.5 | 406.2 +/− 46.2 | 409.5 +/− 34.3 |
| 160-mg | | | 422.8 +/− 27.9 |

QTc changes > 60 msec: serious; QTc changes > 30 msec: questionable

Laboratory evaluations were collected at the time points listed in Table 1. All safety clinical laboratory testing was performed by a central laboratory, with the exception of the urine pregnancy test and methemoglobin which was completed on-site. Specimen samples were sent from the investigative site to the central laboratory. A urine pregnancy test was performed at the time points listed in Table 1 if any woman was not surgically sterilized or post-menopausal.

Clinical Labs were performed with subjects fasting and include the following: Urinalysis: Protein dipstick, specific gravity, appearance, pH, glucose, blood, bilirubin, ketones, and microscopic examination. Clinical chemistry panel included: albumin, alkaline phosphatase, serum amylase, ALT, AST, BUN, calcium (serum), serum chloride, CO2, serum creatinine, direct bilirubin, Gamma-GT, glucose, LDH, serum phosphorus, potassium, sodium, total bilirubin, total protein, uric acid, total cholesterol, LDL, HDL, triglycerides, and HbA1c (Screening only). Hematology panel included: WBC, RBC, Hb, Hct, MCV, MCH, MCHC, Platelets, RDW.

Female subjects in this study who were not post-menopausal or sterilized were required to be using of the following methods of birth control: total abstinence defined as sexual inactivity which is consistent with the preferred and usual lifestyle of the subject, periodic abstinence (e.g., calendar, ovulation, sympothermal, post-ovulation methods) and withdrawal were not acceptable, male partner sterilization prior to the female subject's entry into the study; and this male is the sole partner for the subject, double barrier method defined as condom and occlusive cap (diaphragm or cervical/vault caps) plus spermicidal agent (foam/gel/film/cream/suppository) combined with pharmaceutical contraception listed below:
  Oral contraception, either combined or progestogen alone
  Injectable progestogen
  Implants of levonorgestrel
  Estrogenic vaginal ring
  Percutaneous contraceptive patches
  Intrauterine device (IUD) or intrauterine system (IUS) that meets the <1% failure rate as stated on the product label Any subject who becomes pregnant during the study was not eligible to continue in the study and completed end of study procedures at that time. Male subjects and their partners were expected to use appropriate birth control methods or abstain from sexual intercourse. Male subjects agreed to inform the Investigator immediately if their partner becomes pregnant during the course of the study monitoring period.

Complete pregnancy information, including the outcome of the pregnancy, was collected in the source documents on any female subject or partner of a male subject (if she was willing) who became pregnant during this study monitoring period. In the absence of complications, follow-up will be no longer than 6 to 8 weeks following the delivery date. Any premature terminations, whether elective, therapeutic, or spontaneous, were reported. While pregnancy itself was not considered to be an adverse effect, any pregnancy complications, including a spontaneous termination or elective termination for medical reasons, should be reported as an adverse effect. A spontaneous abortion was considered to be an SAE. Any SAE occurring as a result of a post-study pregnancy and considered reasonably related to the investigational product by the Investigator was reported to the Sponsor.

As defined by the International Conference on Harmonisation (ICH), an AE was any untoward medical occurrence in a patient or clinical investigation subject administered an investigational product, whether or not the event was considered related to the investigational product. An AE was therefore any unfavorable and unintended sign (including an abnormal laboratory finding), symptom, or disease (new or exacerbated) temporally associated with the use of the investigational product and was collected starting when IP was administered. Examples of an AE included conditions newly detected or diagnosed after investigational product administration, including conditions that may have been present but undetected prior to the start of the study, conditions known to have been present prior to the start of the study which worsen after the administration of the investigational product, signs, symptoms, or the clinical sequelae of a suspected drug interaction, and signs, symptoms, or the clinical sequelae of a suspected overdose of either investigational product or a concurrent medication (overdose per se was not reported as an AE). Examples of issues not considered an AE included: medical or surgical procedures (e.g., endoscopy, appendectomy); a condition that leads to a procedure is an AE if it qualifies according to the definitions above, situations where an untoward medical occurrence has not occur (e.g., social, observational, diagnostic, or convenience admission to a hospital), fluctuations of pre-existing disease(s) or condition(s) present or detected at the start of the study that do not represent a clinically significant exacerbation, and abnormal laboratory or test findings that were not assessed by the PI or a sub-Investigator with appropriate medical training as clinically significant. A summary of adverse events is detailed in Table 8.

TABLE 8

Summary of Adverse Events

|  | Placebo | 40 mg | 80 mg |
|---|---|---|---|
| Overall: | | | |
| Number (%) of Subjects with at least one AE | 9(50.0%) | 12(63.2%) | 14(7738%) |
| Number (%) of Subjects with at least one TEAE | 9(50.0%) | 12(63.2%) | 14(7738%) |
| Number of AEs | 15 | 32 | 40 |
| Number of TEAEs | 15 | 32 | 39 |
| Number of SAEs | 2 | 0 | 0 |
| Number of TEAEs by Severity | | | |
| Mild | 12 | 26 | 31 |
| Moderate | 3 | 6 | 8 |
| Number of TEAEs by Relationship to Study Drug | | | |
| Not Related | 12 | 10 | 9 |
| Possibly Related | 3 | 22 | 24 |
| Probably Related | 0 | 0 | 6 |
| Six-Day Dose-Escalation Period Only: | | | |
| Number (5) of Subjects with at least one TEAE | 2(11.1%) | 3(15.8%) | 7(38.9%) |
| Number of TEAEs | 2 | 3 | 11 |

Statistical Methods

Demographic data, clinical chemistry, CBCs, biomarkers, and adverse events were summarized in tabular form by dose level and overall. Descriptive statistics were used to summarize the demographic and clinical data, such as ECGs and vitals. Laboratory values above and below the normal limit were flagged, and adverse events presented by SOC, severity and relationship to study treatment.

The primary efficacy analysis was compare to the change from baseline and Day 70 (Visit 6) of FMD between the pooled-drug and placebo treated groups following 10 weeks of treatment using an unpaired t-test. In case of a substantially skewed distribution within the comparison groups, a nonparametric two sample Wilcoxon signed-rank test was used. For dichotomized efficacy endpoints the null hypothesis H0: rc=rp versus H1: rc≠rp was tested, where rc is the proportion of subjects with improved results in BID cohort and rp was the proportion of subjects with improved results in the placebo cohort. The differences between groups were tested with chi square test or Fisher exact test. Secondary analyses employed repeated measures ANOVA based on Generalized Estimating Equations to incorporate time, group and interaction. Other confounding variables were included in the baseline covariates framework. Analysis of the secondary endpoints such as 6-minute walk and QoL questionnaires was performed as described for the primary efficacy analysis. All statistical decisions were made before un-blinding.

Additionally, plasma levels of sodium nitrite were tabulated and plotted as a log-dose response curve. Functional parameters were tabulated by dose and overall. Summary statistics were computed and log-dose response curves were prepared for each parameter as appropriate.

A statistical analysis plan was developed to detail the statistical approach, particular contrasts of interest, and additionally include any exploratory or unadjusted analysis of the primary efficacy endpoints by treatment group.

With a total sample size of 50 subjects (n=34 sodium nitrite; n=16 placebo), the study had ~82% power to detect a difference in the means of sodium nitrite (pooled-groups) compared with placebo for the efficacy endpoint of FMD at the 0.050 two-sided level of significance. Specifically, with approximately 34 subjects in the pooled sodium nitrite group and 16 subjects in the placebo group, the study had 82.19% power to detect a 1.4% difference in FMD responses between sodium nitrite treated subjects compared with placebo treated subjects after 10 weeks of treatment with 1.6% standard deviations (SD). The sample size was thus empirically determined to be sufficient for this early-stage, clinical study. Accounting for drop-outs, a sample size of up to 60 subjects (20 subjects/group) was sufficient to account for drop-outs as needed to achieve a final sample size of approximately 17 subjects per group. Last observation carried forward (LOCF) was applied to missing data.

Example 2

Clinical Studies of Pain Assessment in Specific Patient Populations

Study Rationale and Summary

As described in Example 1, sodium nitrite was investigated as a new therapy for improving function in subjects with PAD. During the assessment of efficacy, quality of life (QoL) questionnaires were conducted which showed that the group of subjects taking 40 mg of sodium nitrite showed significant improvement in pain. The overall goal of this dose-ranging study is therefore to evaluate the improvement in different areas of pain associated with administration of multiple doses of oral sodium nitrite to particular patient populations (e.g., subjects with PAD, diabetic peripheral neuropathy, or subjects with any of the neuropathic pain described herein).

The primary objective of this clinical study is to assess the efficacy of sodium nitrite in reduction of neuropathic pain and the safety and tolerability of multiple doses of twice daily 40 mg and 80 mg sodium nitrite compared with placebo over a defined treatment period. In this study, multiple assessments of biological pain activity and symptoms associated with pain are made during standardized tests. The assessments include: nerve conduction studies, neurosensory testing, pain inventory, functional status assays, and pain surveys.

The subject endpoints include: brief pain inventories, pain diaries, depression and functional status surveys, and neuropathic pain surveys collected from the subjects participating in the studies. The objective endpoints include: nerve conduction studies, physical exams, two-point discrimination test, neurosensory testing via physical exams. Each subject participating in the study will receive pulse oximetry through the study monthly to demonstrate lack of methemoglobinemia.

The trial type is a randomized, double-blind, placebo-controlled, dose ranging, parallel design multiple dosing study targeted on particular patient populations (e.g., subjects with PAD, diabetic peripheral neuropathy, or subjects with any of the neuropathic pain described herein). The trial may have three arms with approximately ten subjects in each arm. Subjects are assigned to either the placebo or sodium nitrite treatment group in accordance with the randomization schedule generated prior to the start of the study. Subjects are randomized into the study to receive one of the treatment regimens of either placebo, 40 mg BID or 80 mg BID of the investigational product of Example 1 is used in these clinical studies.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A method of treating or reducing neuropathic pain, wherein said neuropathic pain does not originate with an initial trauma/injury or infection, said method consisting of orally administering to a subject in need thereof a tablet or capsule formulated for sustained release of inorganic nitrite, said tablet or capsule consisting of about 40 mg of inorganic nitrite or a pharmaceutically acceptable salt thereof and one or more pharmaceutically acceptable excipient, wherein said inorganic nitrite is administered twice daily for a duration sufficient to treat or reduce neuropathic pain.

2. The method of claim 1, further comprising monitoring whether the subject experiences reduced neuropathic pain.

3. The method of claim 2, wherein reduced neuropathic pain is measured as a decrease in pain intensity, frequency, duration, and/or improvements in quality of life.

4. The method of claim 1, wherein said subject has type 1 or type 2 diabetes.

5. The method of claim 1, wherein said subject has chronic neuropathic pain.

6. The method of claim 5, wherein said chronic neuropathic pain is associated with lower back pain, arthritis, headache, multiple sclerosis, fibromyalgia, nerve damage, or cancer.

7. The method of claim 1, wherein said neuropathic pain is selected from the group consisting of diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathy mono-neuropathies, and central pain syndrome.

8. The method of claim 7, wherein said neuropathic pain is diabetic peripheral neuropathy.

9. The method of claim 1, wherein said inorganic nitrite is $KNO_2$.

10. The method of claim 9, wherein said inorganic nitrite is $NaNO_2$.

11. The method of claim 1, wherein said tablet or capsule is administered for at least ten days.

12. The method of claim 1, wherein the reduction in neuropathic pain is assessed by conducting Quality of Life (QoL) Questionnaires.

13. The method of claim 12, wherein said QoL Questionnaire is a Walking Impairment Questionnaire (WIQ) or a RAND 36-Item Short Form Health Survey (RAND 36).

14. The method of claim 13, wherein said WIQ or RAND 36 measure changes in physical functioning, energy/fatigue in physical health, improvement in pain, general health, emotional well being, or social functioning.

15. The method of claim 14, wherein, following administration of said tablet or capsule, said subject exhibits an improvement in said physical functioning, energy/fatigue in physical health, improvement in pain, general health, emotional well being, or social functioning compared to a subject not administered said tablet or capsule.

* * * * *

UNITED STATES PATENT AND TRADEMARK OFFICE
CERTIFICATE OF CORRECTION

PATENT NO. : 9,561,249 B2  
APPLICATION NO. : 14/626571  
DATED : February 7, 2017  
INVENTOR(S) : Christopher Kevil et al.

Page 1 of 1

It is certified that error appears in the above-identified patent and that said Letters Patent is hereby corrected as shown below:

In the Claims

Column 40, Line 41, replace "method of claim 9" with --method of claim 1--;
    Line 52, replace "36measure" with --36 measure--.

Signed and Sealed this
Seventeenth Day of October, 2017

Joseph Matal
*Performing the Functions and Duties of the
Under Secretary of Commerce for Intellectual Property and
Director of the United States Patent and Trademark Office*